United States Patent
Swartz et al.

(10) Patent No.: US 10,821,056 B2
(45) Date of Patent: *Nov. 3, 2020

(54) FOAMING ORAL CARE COMPOSITIONS

(71) Applicant: The Procter & Gamble Company, Cincinnati, OH (US)

(72) Inventors: Jeanette Marie Swartz, Loveland, OH (US); Arif Ali Baig, Mason, OH (US); Gregory Charles Gordon, Loveland, OH (US); Min Mao, Deerfield Township, OH (US); Melissa Cherie Payne, West Chester, OH (US); Holly Balasubramanian Rauckhorst, Ft. Thomas, TX (US); Paul Albert Sagel, Maineville, OH (US); Paul Dennis Trokhan, Hamilton, OH (US); Brian Patrick Croll, Hamilton, OH (US); Dinah Achola Nyangiro, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,176

(22) Filed: May 14, 2019

(65) Prior Publication Data
US 2019/0343735 A1  Nov. 14, 2019

Related U.S. Application Data

(60) Provisional application No. 62/671,066, filed on May 14, 2018, provisional application No. 62/671,072, filed on May 14, 2018, provisional application No. 62/671,078, filed on May 14, 2018, provisional application No. 62/671,083, filed on May 14, 2018.

(51) Int. Cl.
| | |
|---|---|
| *A61K 8/02* | (2006.01) |
| *A61Q 11/00* | (2006.01) |
| *A61K 8/20* | (2006.01) |
| *A61K 8/21* | (2006.01) |
| *A61K 8/46* | (2006.01) |
| *A61K 8/41* | (2006.01) |
| *A61K 8/25* | (2006.01) |
| *A61K 8/81* | (2006.01) |
| *A61K 8/27* | (2006.01) |
| *A61K 8/04* | (2006.01) |
| *A61K 8/19* | (2006.01) |
| *A61K 8/34* | (2006.01) |
| *A61K 8/44* | (2006.01) |
| *A61K 8/60* | (2006.01) |
| *A61K 8/24* | (2006.01) |
| *A61K 8/36* | (2006.01) |

(52) U.S. Cl.
CPC ............ *A61K 8/0204* (2013.01); *A61K 8/046* (2013.01); *A61K 8/19* (2013.01); *A61K 8/20* (2013.01); *A61K 8/21* (2013.01); *A61K 8/25* (2013.01); *A61K 8/27* (2013.01); *A61K 8/345* (2013.01); *A61K 8/416* (2013.01); *A61K 8/442* (2013.01); *A61K 8/463* (2013.01); *A61K 8/60* (2013.01); *A61K 8/8129* (2013.01); *A61Q 11/00* (2013.01); *A46B 2200/1066* (2013.01); *A61K 8/24* (2013.01); *A61K 8/347* (2013.01); *A61K 8/36* (2013.01); *A61K 2800/28* (2013.01); *A61K 2800/882* (2013.01); *A61K 2800/92* (2013.01); *A61K 2800/95* (2013.01)

(58) Field of Classification Search
None
See application file for complete search history.

(56) References Cited

U.S. PATENT DOCUMENTS

| | | |
|---|---|---|
| 3,964,166 A | 6/1976 | Stahlman |
| 4,157,386 A | 6/1979 | La Rochelle |
| 4,267,164 A | 5/1981 | Yeh |
| 4,765,984 A | 8/1988 | Vellekoop |
| 6,521,216 B1 | 2/2003 | Glandorf |
| 6,555,094 B1 | 4/2003 | Glandorf |
| 6,685,920 B2 | 2/2004 | Baig |
| 6,696,045 B2 | 2/2004 | Yue |
| 6,713,049 B1 | 3/2004 | White |
| 7,387,774 B2 | 6/2008 | Faller |
| 8,071,076 B2 | 12/2011 | Nathoo |
| 8,113,729 B2 | 2/2012 | Solan |
| 8,211,409 B2 | 7/2012 | Baig |
| 8,728,446 B2 | 5/2014 | Hurwitz |

(Continued)

FOREIGN PATENT DOCUMENTS

| | | |
|---|---|---|
| EP | 1438953 A1 | 7/2004 |
| EP | 2431028 A2 | 3/2012 |

(Continued)

OTHER PUBLICATIONS

All Office Actions for U.S. Appl. No. 16/411,178, filed May 14, 2019.
All Office Actions for U.S. Appl. No. 16/411,180, filed May 14, 2019.
All Office Actions for U.S. Appl. No. 16/411,181, filed May 14, 2019.
U.S. Appl. No. 16/411,178, filed May 14, 2019, Mao et al.
U.S. Appl. No. 16/411,181, filed May 14, 2019, Payne et al.
U.S. Appl. No. 16/411,181, filed May 14, 2019, Baig et al.
PCT Search Report and Written Opinion for PCT/US2019/032084 dated Aug. 8, 2019.

(Continued)

*Primary Examiner* — Celeste A Roney
(74) *Attorney, Agent, or Firm* — Parker D. McCrary

(57) ABSTRACT

Oral care compositions and/or unit-dose oral care compositions comprising a high level of surfactant. Oral care compositions and/or unit-dose oral care compositions with a high foaming efficiency. Oral care compositions and/or unit-dose oral care compositions with one or more web forming materials, one or more surfactants, and a sugar alcohol.

14 Claims, 4 Drawing Sheets

(56) References Cited

U.S. PATENT DOCUMENTS

| | | |
|---|---|---|
| 8,785,361 B2 | 7/2014 | Sivik |
| 8,827,583 B2 | 9/2014 | Solan |
| 8,980,816 B2 | 3/2015 | Dreher |
| 9,074,305 B2 | 7/2015 | Glenn, Jr. |
| 9,139,802 B2 | 9/2015 | Weisman |
| 9,163,205 B2 | 10/2015 | Sivik |
| 9,175,250 B2 | 11/2015 | Sivik |
| 9,492,379 B2 | 11/2016 | Park |
| 9,545,364 B2 | 1/2017 | Glenn, Jr. |
| 9,656,102 B2 | 5/2017 | Vaccaro |
| 9,750,669 B2 | 9/2017 | Solan |
| 9,801,830 B2 | 10/2017 | Darcy |
| 10,092,779 B2 | 10/2018 | Fontana |
| 10,226,410 B2 | 3/2019 | Yang |
| 10,258,549 B2 | 4/2019 | Baig |
| 10,258,550 B2 | 4/2019 | Baig |
| 10,285,921 B2 | 5/2019 | Chen |
| 2002/0127190 A1 | 9/2002 | Zerbe |
| 2005/0137272 A1 | 6/2005 | Gaserod |
| 2006/0039958 A1 | 2/2006 | Fuisz |
| 2010/0150848 A1* | 6/2010 | Baig ............... A61K 8/25 424/55 |
| 2011/0027328 A1 | 2/2011 | Baig |
| 2012/0027838 A1 | 2/2012 | Gordon |
| 2012/0052036 A1 | 3/2012 | Glenn, Jr. |
| 2012/0058166 A1 | 3/2012 | Glenn, Jr. |
| 2012/0175273 A1* | 7/2012 | Jacobs ............. A61K 8/9789 206/63.5 |
| 2012/0237576 A1 | 9/2012 | Gordon |
| 2013/0171421 A1 | 7/2013 | Weisman et al. |
| 2013/0302387 A1 | 11/2013 | Pedersen |
| 2014/0314692 A1 | 10/2014 | Vaccaro |
| 2015/0071572 A1 | 3/2015 | Dreher |
| 2015/0072915 A1 | 3/2015 | Dreher |
| 2015/0159330 A1 | 6/2015 | Weisman et al. |
| 2015/0209469 A1 | 7/2015 | Mckiernan |
| 2015/0297494 A1 | 10/2015 | Mao |
| 2016/0101026 A1 | 4/2016 | Pratt |
| 2016/0101204 A1 | 4/2016 | Lynch |
| 2016/0258083 A1 | 9/2016 | Weisman |
| 2017/0135919 A1 | 5/2017 | Yang |
| 2017/0211207 A1 | 7/2017 | Sivik |
| 2017/0281490 A1 | 10/2017 | Ramji |
| 2018/0216285 A1 | 8/2018 | Pratt |
| 2018/0216286 A1 | 8/2018 | Glassmeyer |
| 2018/0216287 A1 | 8/2018 | Weisman |
| 2018/0216288 A1 | 8/2018 | Weisman |
| 2018/0334642 A1 | 11/2018 | Hodgdon |
| 2018/0334643 A1 | 11/2018 | Hamersky |
| 2018/0334644 A1 | 11/2018 | Hamersky |

FOREIGN PATENT DOCUMENTS

| | | | |
|---|---|---|---|
| EP | 2940205 A1 | 11/2015 | |
| GB | 2373439 A | 9/2002 | |
| GB | 2436463 A | 9/2007 | |
| NL | 1009030 C1 * | 11/1999 | ............ A61Q 11/00 |
| WO | WO1999033437 A1 * | 12/1999 | ............ A61K 7/16 |
| WO | WO2004047784 A1 | 6/2004 | |
| WO | WO2009022761 A1 | 2/2009 | |
| WO | WO2009029352 A1 | 3/2009 | |
| WO | WO2011053291 A1 | 5/2011 | |
| WO | WO2015095932 A1 | 7/2015 | |
| WO | WO2016057353 A1 | 4/2016 | |
| WO | WO2016156161 A1 | 10/2016 | |
| WO | WO2017079956 A1 | 5/2017 | |

OTHER PUBLICATIONS

PCT Search Report and Written Opinion for PCT/US2019/032085 dated Jul. 30, 2019.

PCT Search Report and Written Opinion for PCT/US2019/032086 dated Aug. 8, 2019.

PCT Search Report and Written Opinion for PCT/US2019/032126 dated Aug. 13, 2019.

Anonymous: Toothpaste Tablets retried from www.gnpd.com; Database accession No. 1073814 dated Dec. 8, 2018.

Mintel: Cool Mint Breath Strips from www.gnpd.com dated Jan. 1, 2008.

* cited by examiner

FOAMING ORAL CARE COMPOSITIONS

FIELD OF THE INVENTION

The present invention relates to oral care compositions comprising high levels of surfactant. The present invention also relates to unit-dose oral care compositions comprising high levels of surfactant. The present invention also relates to oral care compositions and/or unit-dose oral care compositions with a high foaming or cleaning efficiency.

BACKGROUND OF THE INVENTION

Dentifrice compositions are typically formulated as a paste that can be squeezed out of a tube. Dentifrice compositions can include metal ions, fluoride ions, abrasives, calcium sources, surfactants, whitening agents, humectants, thickening agents, and other formulation ingredients. Typically, dentifrice compositions must be carefully formulated to avoid reactivity in the tube, but retain reactivity in the oral cavity. In many cases, ingredients must be substituted or removed to balance reactivity in the tube with in mouth benefits.

One dentifrice component that can be manipulated are surfactants. Surfactants are commonly used in dentifrice compositions to generate foam, remove plaque, and to stabilize the remaining components of the dentifrice in the dentifrice tube and in the mouth upon application. Many consumers perceive the generation of foam during the application of dentifrice with a toothbrush as an irresistible and pleasant experience. Foam in a dentifrice can ensure an even distribution of polishing, enamel-strengthening, and other active ingredients during cleaning.

Foam can also be generated with different pore sizes depending on the exact formulations used. Thus, foaming behavior is a key quality characteristic in the formulation of toothpastes. Moreover, the proper density, volume, and pore-size of foam can allow for a better distribution of cleaning and oral care active ingredients. However, paste dentifrice compositions can only have certain proportions of surfactant due to the reactivity of the surfactant and high levels of surfactant lead to unfavorable physical properties. As such, the present invention is directed to oral care compositions that can allow for the incorporation of high levels of surfactant.

SUMMARY OF THE INVENTION

Disclosed herein is a unit-dose oral care composition comprising (a) one or more web forming materials; (b) one or more surfactants; and (c) a sugar alcohol.

Disclosed herein is an oral care composition comprising (a) one or more nonwoven web layers comprising (i) one or more web forming materials, (ii) one or more surfactants, and (iii) a sugar alcohol; and (b) a nonfibrous composition, the nonfibrous composition comprising an abrasive.

Disclosed herein is an oral care composition comprising a nonwoven web composition, the nonwoven web composition comprising (a) from about 0.01% to less than 10%, by weight of the oral care composition, of one or more web forming materials; (b) from about 5% to about 20%, by weight of the oral care composition, of one or more surfactants; and (c) from about 10% to about 50%, by weight of the oral care composition, a sugar alcohol.

Disclosed herein is a method of brushing at least one tooth with the compositions disclosed herein.

DETAILED DESCRIPTION OF THE INVENTION

Figure 1:
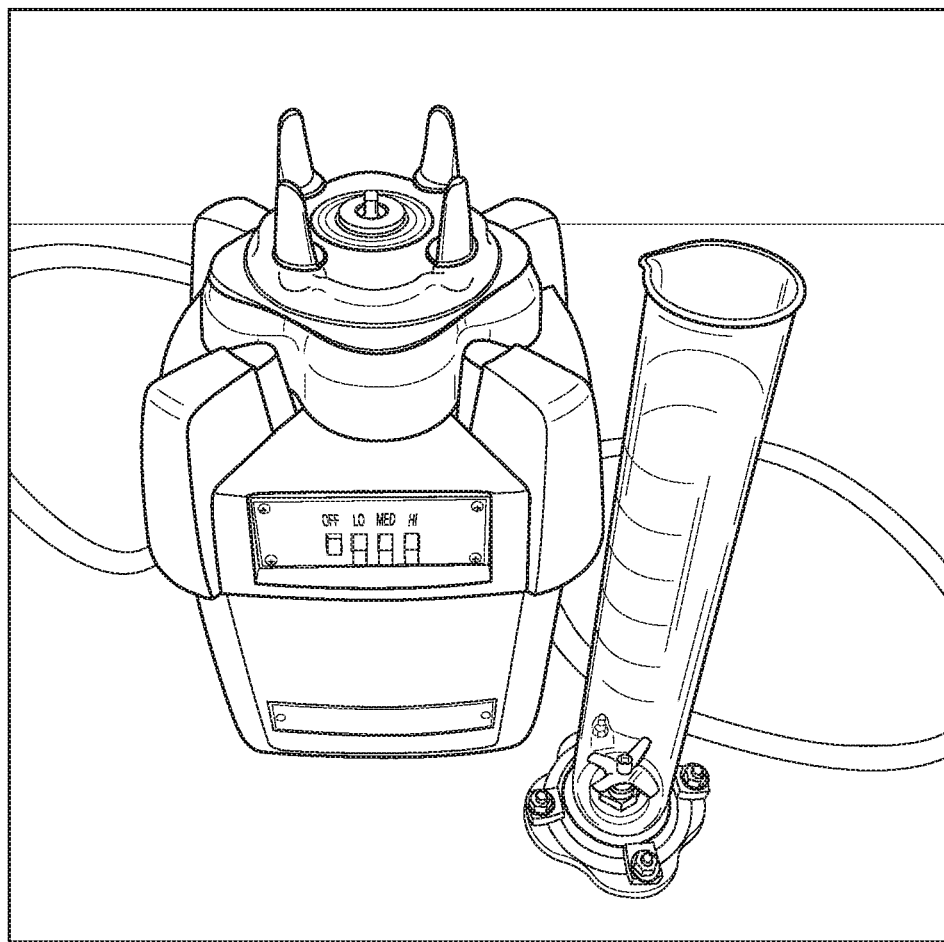
FIG. 1 is a photograph illustrating the foam height measurement device.

The present invention relates to oral care compositions with a high cleaning ability and/or high foaming efficiency. The present invention also relates to unit-dose oral care compositions with a high cleaning ability and/or high foaming efficiency. The present invention also relates to oral care compositions and/or unit-dose oral care compositions with a high surfactant level.

Surfactants can be difficult to formulate in oral care compositions due to reactivity with other ingredients in the oral care compositions and/or the impact of high levels of surfactants on the physical properties of oral care compositions. Surfactants impact technical benefits, such as imparting cleaning benefits to the oral cavity and/or solubilizing other ingredients to be effectively applied to the oral cavity, and consumer experience benefits, such as a providing foam. Thus, it would be advantageous to provide an oral care composition with a cleaning ability and/or high foaming efficiency.

The present invention is directed to oral care compositions that use assembled design to physically separate surfactants from other reactive components of the oral care composition. For example, the surfactants can be in one location of the oral care composition and other components can in a separate location of the oral care composition. Additionally, the surfactant can be formulated in the solid phase, either spun into the fibrous composition or added to the nonfibrous composition, which can mitigate the impact of high levels of surfactants on the physical properties of oral care compositions. While dentifrice reactivity is typically manipulated through formulation design, the use of nonwoven webs comprising soluble fibers will allow for reactivity to be dramatically lowered by separating components by placing them in the solid phase, where reactivity is lower, or physically separating the ingredients through assembly design of the oral care composition.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition" as used herein means a product that in the ordinary course of usage is retained in the oral cavity for a time sufficient to contact some or all of the dental surfaces and/or oral tissues for purposes of oral health. In one embodiment, the composition is retained in the oral cavity to deliver an oral care active agent. The oral composition of the present invention may be in various forms including toothpaste, dentifrice, tooth gel, tooth powders, tablets, rinse, sub gingival gel, foam, mousse, chewing gum, lipstick, sponge, floss, prophy paste, petrolatum gel, denture product, nonwoven web, or foam. In one embodiment, the oral composition is in the form of a nonwoven web. In another embodiment, the oral composition is in the form of a dentifrice. The oral composition may also be incorporated onto strips or films for direct application or attachment to oral surfaces or incorporated into floss. The oral care composition may also be a strip that can be directly applied to a surface of the oral cavity. The strip can at least partially dissolve upon contact with moisture or brushing.

The term "orally acceptable carrier" as used herein means a suitable vehicle or ingredient, which can be used to form and/or apply the present compositions to the oral cavity in a safe and effective manner.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. Depending on the type of oral health benefit and the efficacy of active compound, "effective amount" means at least about 0.0001% of the material, 0.001% of the material, or 0.01 of the material, by weight of the composition.

The term "dentifrice" as used herein means paste, gel, powder, tablets, or liquid formulations, unless otherwise specified, that are used to clean, treat, or contact the surfaces of the oral cavity. Additionally, as disclosed herein, the dentifrice means a nonwoven web that are used to clean the surfaces of the oral cavity. The term "teeth" as used herein refers to natural teeth as well as artificial teeth or dental prosthesis.

As used herein, the term "filament" means a thin, flexible threadlike object that can be used to form a nonwoven web of the present type. The length of a filament can greatly exceed its diameter, i.e. a length to diameter ratio of at least about 5, 10, or 25.

The filaments of the present invention may be spun from nonwoven web forming materials via suitable spinning operations, such as meltblowing or spunbonding.

Filaments are typically considered continuous or substantially continuous in nature. Filaments are relatively longer than fibers. Non-limiting examples of filaments can include meltblown filaments, spunbond filaments, and combinations thereof. In one embodiment, the filaments are meltblown filaments.

In one example, the filaments may be in the form of fibers, such as when the filaments are cut to shorter lengths. Thus, in one example, the present invention also includes a fiber comprising the composition of the filament of the present invention.

As used herein, "nonwoven web forming material" means a composition that is suitable for making a filament such as by meltblowing, spunbonding, or fluid film fibrillation. The nonwoven web forming material comprises one or more nonwoven web forming materials that exhibit properties that make them suitable for spinning into a filament.

As used herein, "length", with respect to a filament, means the length along the longest axis of the filament from one terminus to the other terminus. If a filament has a kink, curl or curves in it, then the length is the length along the entire path of the filament.

As used herein, "average diameter", with respect to a filament, is measured according to the Diameter Test Method described herein.

As used herein, the term "disintegratable" and "disintegration" means that the oral care composition, filament, or nonwoven is reduced to components, fragments or compositions when exposed to conditions of intended use.

As used herein, the term "dissolves" means that the oral care composition, filament, or nonwoven web is mostly or completely solubilized. The oral care composition may appear to visibly dissolve even though some of the components do not completely dissolve—for example cross linked polyacrylic acid polymers form clear gels giving the appearance of dissolution while, not wishing to be bound by theory, the clear gels are simply hydrated. Another example is an abrasive which does not dissolve at all even though it may make up the majority of the composition. An oral composition comprising an abrasive would still be deemed to be "dissolved" if only the abrasive has not dissolved. Dissolution of the oral care composition is complete when any remaining particles have a diameter of 2 mm or less.

As used herein, the term "applying" includes spraying, dusting, sprinkling, coating, surface-printing (e.g., in the shape of a desired adornment, decoration, or pattern), pouring on, injecting into the interior, dipping, or by any other suitable means, such as by use of a depositor, sifter, or powder bed.

As used herein, "conditions of intended use" means the temperature, physical, chemical, and/or mechanical conditions that an oral care composition comprising one or more filaments of the present invention is exposed to when the oral care composition is used for its designed purpose. The oral care compositions of the present invention can be administered to a mammal via the oral cavity, mouth, throat, and combinations thereof. The conditions of intended use can be the temperature, physical, chemical, and/or mechanical conditions in the oral cavity, mouth, and/or throat of a mammal.

"Triggering condition" as used herein means anything, as an act or event that serves as a stimulus and initiates or precipitates a change in the filament, such as a loss or altering of the filament's physical structure and/or a release an oral care active including dissolution, hydration, and swelling. Some triggering conditions include a suitable pH, temperature, shear rate, or water content.

"Morphology changes" as used herein with respect to a filament's morphology changing means that the filament experiences a change in its physical structure. Non-limiting examples of morphology changes for a filament of the present invention include dissolution, melting, swelling, shrinking, breaking into pieces, lengthening, shortening, peeling, splitting, shredding, imploding, twisting, and combinations thereof. The filaments of the present invention may completely or substantially lose their filament physical structure or they may have their morphology changed or they may retain or substantially retain their filament physical structure as they are exposed to conditions of intended use.

As used herein, a "web" means a sheet of continuous filaments or fibers of any nature or origin that have been formed into a web by any means, and bonded together by any means.

As used herein and as defined by European Disposables and Nonwovens Association (EDANA), "nonwoven web" means a sheet of continuous filaments or fibers of any nature or origin that have been formed into a web by any means, and bonded together by any means, with the exception of weaving or knitting. Felts obtained by wet milling are not nonwovens. In one example, a nonwoven web according to the present invention means an orderly arrangement of filaments within a structure in order to perform a function. In one example, a nonwoven web of the present invention is an arrangement comprising a plurality of two or more and/or three or more filaments that are inter-entangled or otherwise associated with one another to form a nonwoven web.

The term RDA refers to Relative Dentin Abrasion or Radioactive Dentin Abrasion as defined in FDI-ISO 11609. The term PCR refers to Pellicle Cleaning Ratio as defined in the original paper by Stookey et al. 1982 and later used by Schemehorn et al. 2011 to characterize the relative effectiveness of oral care compositions to remove a laboratory-sourced, human-like, stain from enamel chips. These experimental techniques will be described in greater detail later.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated. All measurements referred to herein are made at 25° C. unless otherwise specified.

The composition, process and methods of the present invention can comprise, consist of, or consist essentially of, the essential elements and limitations of the invention described herein, as well as any additional or optional ingredients, components, or limitations described herein or otherwise useful in oral care compositions intended for use or consumption by mammals preferably consumption or use by humans.

Unit-Dose Oral Care Composition

The oral care compositions of the present invention can be unit-dose oral care compositions. A unit-dose oral care composition is an amount of the oral care composition to be administered to a patient or consumer in a single use. The unit-dose oral care composition can be a unit-dose dentifrice, a unit-dose mouth rinse, a unit-dose tooth gel, a unit-dose tooth whitening composition, or any other suitable unit-dose oral care composition capable of being retained in the oral cavity for a time sufficient to contact some or all of the dental surfaces and/or oral tissues for purposes of oral health.

The amount, in mass and/or volume, of the unit-dose oral care composition is determined based on the desired type of unit-dose oral care composition. For example, a unit-dose dentifrice can be sized to deliver the correct amount of fluoride in a single use according to local laws and regulations, such as the U.S. Food and Drug Administration (FDA) monograph, which allows formulations of 850 to 1150 ppm and/or 1500 ppm of fluoride ions. Additionally, a unit-dose dentifrice can be sized to deliver the correct amount or ratio of other ingredients, such as, for example, antimicrobial agents, abrasives, surfactants, flavors, metal ions, etc. Similarly, a unit-dose mouth rinse can be sized to deliver the correct amount of mouth rinse ingredients, such as, for example, fluoride ions, antimicrobial agents, abrasives, surfactants, flavors, metal ions, etc.

The unit-dose oral care composition can be in the form of a pouch, a droplet, a solid open cell foam, a solid closed cell foam, a fibrous composition, a paste composition, a gel composition, a tablet composition, a strip composition, a tape composition, and/or an assembly of one or more of the forms described in this paragraph.

The unit-dose oral care composition can be sized to fit a manual toothbrush, an electric toothbrush, or any other applicator designed to help contact the unit-dose oral care composition to the surfaces of the oral cavity, including, but not limited to teeth.

The unit-dose oral care composition of the present invention can be a substantially flat or flat composition in the form of a pad, strip, tape, or tablet having a thickness of from about 0.05 millimeter (mm) to about 20 mm, from about 0.05 mm to about 10 mm, from about 0.05 mm to about 5 mm, from about 0.5 mm to about 1 mm, from about 0.05 mm to about 0.5 mm, from about 0.05 mm to about 0.25 mm, or from about 0.05 mm to about 0.1 mm, as measured by the Thickness Method described hereafter. The unit-dose oral care composition can be formed into a cylindrical shape (e.g. by rolling) having a length from about 0.5 centimeter (cm) to about 10 cm, from about 1 cm to about 5 cm, or from about 1.5 cm to about 3 cm. The unit-dose oral care composition can be a rectangular prism including a cube wherein the longest sides of the rectangular prism has a length from about 5 mm to 20 mm, from about 10 mm to 15 mm, or from about 5 mm to about 10 mm, as measured by the Thickness Method described herein. If the dimensions of the dose changes, the basis weight of the dose can change. The unit-dose oral care composition can be circular or an oval wherein the diameter of the circle or the length of the longest portion of the oval is from about 5 mm to about 5 cm, 5 mm to about 100 mm, 5 mm to about 50 mm, 1 cm to about 5 cm, or 100 mm to about 1 cm.

The unit-dose oral care composition can be in the form of one or more flat sheets or pads of an adequate size to be able to be handled easily by the user. The unit-dose oral care composition can comprise one unit-dose of one or more oral care actives that can provide one or more oral care benefits and/or treat one or more oral care conditions. The unit-dose oral care composition may have a square, rectangle, oval, circular, disc shape or any other suitable shape. The unit-dose oral care composition can also be in the form of a continuous strip including delivery on a tape-like roll dispenser with individual portions dispensed via perforations and/or a cutting mechanism.

A unit-dose oral care composition can allow for the dose to include incompatible components within the same composition. Components are considered incompatible with one another, if when they are in the same solution or as non-solid mixtures, at least one of the components has a significant reduction in efficacy, stability, or bioavailability. Incompatible components can be components that chemically interact with each other to form new compounds, complexes and/or salts and/or components that will separate into discrete portions or phases of the composition to minimize unfavorable interactions.

Examples of incompatible components can include, but are not limited to, metal ion sources and silica abrasives, metal ion sources and polyphosphates, metal ion sources and pyrophosphates, calcium ion sources and fluoride ion sources, calcium ion sources and phosphate salts, calcium ion sources and pyrophosphate, oxalate ions and peroxide compounds, stannous fluoride and peroxide compounds, cationic antimicrobial agents, such as cetyl pyridinium chloride, and fluoride ion sources, acids and bases, calcium ion sources and chelants, such as EDTA, oxidizing agents and reducing agents, hydrophobic components, such as petrolatum, silicones, polybutene, and hydrophilic components, such as water and alcohols, and/or any other incompatible components, as defined above.

The unit-dose oral care compositions, as described herein, can be designed to maximize bioavailability, stability, and/or efficacy of the ingredients by minimizing reactivity between the ingredients. Minimizing reactivity between the ingredients can be accomplished by physically separating the ingredients into discrete portions of the composition or by placing one or more ingredients in the solid phase where reactivity is lower.

In the context of a pouch composition, the interior volume can be separated into multiple discrete, layered, adjacent, and/or superimposed portions that can place one or more components in each portion. For example, a fluoride ion source can be in one portion while a calcium ion source can be in another portion of the pouch composition. Additionally, a metal ion source can be in one portion while a silica abrasive or polyphosphate can be in another portion of the pouch composition.

In the context of a fibrous oral care composition, one or more reactive components can be in a one nonwoven web layer and one or more reactive components can be in another nonwoven web layer. Additionally, one or more reactive components can be in one or more nonwoven web layers and one or more reactive components can be between, on top, below, folded within, adjacent, or superimposed with the one or more nonwoven web layers, such as in a nonfibrous composition. For example, a fluoride ion source can be spun within or commingled with a first fibrous composition comprising one or more nonwoven web layers and a calcium ion source can be spun within or commingled with a second fibrous composition comprising one or more nonwoven web layers. The first and second fibrous compositions can be assembled into a single multi-ply composition using any suitable means. Additionally, a fluoride ion source can be spun within or commingled with a fibrous composition comprising one or more nonwoven web layers and a calcium ion source can be in a nonfibrous composition, as a solid composition or at least partially dissolved or at least partially dispersed in a liquid composition. The fibrous composition and the nonfibrous composition can be assembled into a multi-ply composition or the nonfibrous composition can be can be between, on top, below, folded within, adjacent, or superimposed with the fibrous composition.

In the context of a foam oral care composition, such as a flexible porous dissolvable solid structure, the reactive components can be within or commingled together within an open cell or closed cell foam, the foam compositions are described in US 2011/0027328, which is herein incorporated by reference. One or more reactive components can be in the foam composition, while one or more reactive components can be in a nonfoam composition, such as a surface resident particulate coating, which coats the surface of the solid foam composition.

The use of a unit-dose oral care composition, as described herein, allows for easy portability and the ability to better control dosing. For example, due to current restrictions on airlines regarding liquid products, a passenger is limited to carrying on only a small amount of mouth rinse or dentifrice or to packing his mouth rinse or dentifrice in his checked luggage. If the oral care composition were in unit-dose form, the passenger can pack exactly the amount needed into a carry-on without the need to worry about airline packing restrictions.

Fibrous Oral Care Composition

The oral care composition can be a fibrous oral care composition. The fibrous oral care composition can comprise a fibrous composition and/or a nonfibrous composition. The fibrous composition can comprise at least one web. The fibrous composition can comprise a nonwoven web and/or a woven web.

The fibrous composition can comprise one or more web layers. The one or web layers can comprise one or more filaments and/or fibers. The oral care composition may comprise a first web and a second web wherein the first and the second web comprise different components.

The fibrous composition can comprise any suitable oral care component. The fibrous composition can comprise any component described herein.

The web can comprise more than one filament. The web can comprise a first filament and a second filament both comprising an oral care active and the oral care active can be the same oral care active or different oral care actives. The web can comprise a first filament comprising an immediate delivery oral care active and a second filament comprising an extended delivery, a delayed delivery, and/or a targeted delivery oral care active. The web can comprise a first filament, a second filament, and a third filament, wherein each filament comprises a different oral care component.

The web or oral care composition can comprise a plurality of identical or substantially identical, from a compositional perspective, filaments according to the present invention. The web or oral care composition may comprise two or more different filaments according to the present invention. Non-limiting examples of differences in the filaments may be physical differences such as differences in diameter, length, texture, shape, rigidity, elasticity, and the like; chemical differences such as crosslinking level, solubility, melting point, glass transition temperature (Tg), web forming material, color, amount of oral care active, amount of web forming material, presence of a coating composition on the oral care composition, chemical composition of the oral care active including whether the oral care active is immediate delivery, delayed delivery, extended delivery, or targeted delivery, and the like; differences in whether the filament loses its physical structure when the filament is exposed to conditions of intended use; differences in whether the filament's morphology changes when the filament is exposed to conditions of intended use; and differences in when and where the benefit from the oral care active is experienced. In one example, two or more filaments within the oral care composition or web may comprise the same web forming material, but have different oral care actives.

The web can comprise two or more filaments wherein the filaments release the oral care actives at different rates. The different rates may be caused by the filaments being positioned at an external surface of the web.

The oral care composition can comprise a nonfibrous composition, which may or may not be greater in weight percentage, by weight of the oral care composition, than the fibrous composition. The nonfibrous composition can be between a first web and a second web. At least a portion of the nonfibrous composition can be in contact with a surface of fibrous composition. The nonfibrous composition can be placed on a single web layer and the web layer can be folded on top of the nonfibrous composition, rolled with the nonfibrous composition, placed on top of or below the fibrous composition, and/or the fibrous composition can wrap around the fibrous composition.

The nonfibrous composition can comprise any suitable oral care component. The nonfibrous composition can comprise any component described herein. The nonfibrous composition can be liquid, solid, aqueous, and/or combinations thereof.

The oral care composition of the present invention can have a basis weight of from about 10 grams per square meter (g/m$^2$) to about 5000 g/m$^2$, from about 25 g/m$^2$ to about 2500 g/m², from about 40 g/m² to about 1500 g/m², or from about 500 g/m² to about 2000 g/m².

The fibrous oral care composition can comprise two or more components or oral care actives that are generally considered incompatible, as described herein. For example, a first web layer can comprise a fluoride ion source and a second web layer can comprise a calcium ion source. In another example, a first web layer can comprise a metal ion source, such as a stannous ion source, and a nonfibrous composition can comprise a silica abrasive or a polyphosphate.

The oral care composition or web may exhibit different regions, such as different regions of basis weight, density and/or caliper. The oral care composition or web may comprise discrete regions of filaments that differ from other parts of the web.

The oral care composition or the web may comprise one or more textured, dimpled or otherwise topographically patterned surfaces including letters, logos or figures. The textured oral care composition can result from the shape of the filament or the web, in that the outermost surface of the composition contains portions that are raised with respect to other areas of the surface. The raised portions can result from the formed shape of the oral care composition, for example the web can be formed in a dimpled or waffle pattern. The raised portions can also be the result of creping processes, imprinted coatings, embossing patterns, or the result of the physical form of the composition itself.

The web of the present invention may be pressed into a film to form the oral care composition; this can be done by applying a compressive force and/or heating the web to convert the web into a film. The film can comprise the oral care actives that were present in the filaments of the present invention. The web may be completely converted into a film or parts of the web may remain in the form of a film after partial conversion of the web into the film. The oral care composition may constitute one or more webs wherein at least one of the webs has been pressed into a film. The oral care composition may comprise two or more webs that have been pressed into a film.

The web can be rolled, compressed, cut, or stacked to form a three dimensional oral care composition. For instance, the web may be compressed into a pill or tablet, rolled into a cylinder, or compressed or stacked into a rectangular prism to form the oral care composition.

The oral care composition may constitute one or more layers of webs which are optionally bonded together via a bonding means (including heat, moisture, ultrasonic, pressure etc.). The oral care composition may constitute one or more layers of webs which are optionally bonded together via compression.

The oral care composition or nonwoven web can be perforated with holes or channels penetrating into or through the oral care composition, in total, or locally in one or more web layers. These perforations can be formed as part of making the web or oral care composition via spikes extended from the surface of an adjacent belt, drum, roller or other surface. Alternatively, these perforations can be formed after forming the web or oral care composition by a process of poking or sticking the porous solids with pins, needles or other sharp objects.

Filament

The oral care composition can comprise one or more filaments. In an embodiment, the filaments of the present invention exhibit a length of greater than about 0.1 in., in an alternate embodiment greater than about 0.2 in, in still another embodiment greater than about 0.3 in, and in another embodiment greater than about 2 in.

The filaments can have an average diameter of less than about 150 micrometers (µm), less than about 100 µm, less than about 10 µm, or less than about 1 µm with a relative standard deviation of less than 100%, less than 80%, less than 60%, or less than 50%, such as in the range of 10% to 50%, for example. As set forth herein, the significant number means at least 10% of all the filaments, in another embodiment at least 25% of all the filaments, in another embodiment at least 50% of all the filaments, in yet another embodiment at least 75% of all the filaments. The significant number may be at least 99% of all the filaments. At least 50% of all the filaments may have an average diameter less than about 10 µm. The filaments produced by the method of the present disclosure can have a significant number of filaments with an average diameter less than about 1 µm, or sub-micron filaments. In an embodiment, the oral care composition can comprise at least 25% of all the filaments with an average diameter less than about 1 µm, at least 35% of all the filaments with an average diameter less than about 1 µm, at least 50% of all the filaments with an average diameter less than about 1 µm, or at least 75% of all the filaments with an average diameter less than about 1 µm.

The filament can comprise less than 30% moisture, by weight of the filament, less than 20% moisture, by weight of the filament, less than about 10% moisture, by weight of the filament, less than about 5% moisture, by weight of the filament, less than about 3%, by weight of the filament less than about 1%, or less than about 0.1%, by weight of the filament.

The filament of the present invention can be monocomponent or multicomponent. The filament can be a bicomponent filament. The filament can be a tricomponent filament. The multicomponent filament may be in any form, such as side-by-side, core and sheath, islands-in-the-sea and the like.

The filaments of the present invention may be meltblown filaments. The filaments of the present invention may be spunbond filaments. The filaments may be hollow filaments prior to and/or after release of one or more of its active agents.

The filament may comprise an oral care active within the filament and an oral care active on an external surface of the filament, such as a coating on the filament. The oral care active on the external surface of the filament may be the same or different from the active agent present in the filament. If different, the oral care actives may be compatible or incompatible with one another.

Solid Foam Compositions

The oral care composition can be a solid foam composition, such as the flexible porous dissolve solid structure described in US 2011/0027328, which is herein incorporated by reference. The solid foam composition can be in the form of an open cell foam or a closed cell foam.

The solid foam composition can comprise any suitable oral care component. The solid foam composition can comprise any component described herein. The solid foam composition can comprise a surface resident coating composition. The surface resident coating composition can comprise any suitable oral care component or any component described herein.

Importantly, U.S. Patent Application No. 2011/0027328 does not disclose, teach, or suggest that the amount of pyrophosphate must be minimized in order to produce solid soluble foams. In fact, U.S. Patent Application No. 2011/0027328 only teaches example foam compositions with a high amount of pyrophosphate. As such, it was unexpectedly found here that pyrophosphate interfered with the foam composition formation process.

Thus, the solid foam compositions of the present invention comprise a foam forming material, one or more surfactants, a plasticizer, and wherein the solid foam composition has less than about 5%, less than about 1%, or free of an inorganic metal salt, a polyphosphate, or specifically, a pyrophosphate. The foam forming material is any suitable material that exhibits properties suitable for making a foam. Non-limiting examples of foam forming materials can include the water-soluble polymer disclosed by U.S. Patent Application No. 2011/0027328.

Web Forming Material

The web can be formed by any suitable means. The web can comprise spun fibers and/or spun filaments. The nonwoven web can be made from a web forming material or nonwoven web forming material as described in U.S. patent application Ser. No. 16/250,455, U.S. patent application Ser. No. 16/250,484, U.S. Pat. Nos. 9,139,802, 9,175,250, and/or 8,785,361, which are herein incorporated by reference in their entirety.

The web forming material can comprise any suitable material that exhibits properties suitable for making a fiber or filament. Non-limiting examples of web forming materials can include polymers, polyols, sugars, sugar alcohols, and combinations thereof. The web can comprise two or more different web forming materials. The web can comprise three or more different web forming materials. The polymer can function as a web forming material and in certain embodiments can also provide an oral health benefit.

The fibrous composition can comprise from about 1% to about 100%, from about 2% to about 50%, from about 5% to about 35%, from about 5% to about 20%, from about 1% to about 15%, or from about 5% to about 10% of a nonwoven web forming material, by weight of the fibrous composition.

The oral care composition can comprise from about 1% to about 80%, from about 1% to about 50%, from about 1% to about 25%, from about 2% to about 20%, from about 3% to about 15%, less than about 10%, or from about 5% to about 10% of a web forming material by total weight of the oral care composition.

Polymer

The oral care composition can comprise a polymer. The web forming material can comprise a polymer. The fibrous composition or the nonfibrous composition can comprise a polymer. The foam composition can comprise a polymer. Non-limiting examples of polymers can include naturally sourced polymers, synthetic polymers, and combinations thereof.

Non-limiting examples of naturally sourced polymers can include alginates, gums, protein-based polymers, starch-based polymers, native starches, modified starches, fiber polymers, other naturally sourced polymers, and combinations thereof.

Non-limiting examples of alginates can include ammonium alginate, calcium alginate, potassium alginate, propylene glycol alginate, and combinations thereof.

Non-limiting examples of gums can include acacia gum, carrageenan, tragacanth gum, guar gum, locust bean gum, xanthan gum, gellan gum, and combinations thereof.

Non-limiting examples of protein-based polymers can include whey protein isolate, soy protein isolate, egg albumin, casein, collagen, glutelin, gelatin, gluten, zein, and combinations thereof.

Non-limiting examples of starch-based polymers can include those starch-based polymers sourced from cereals, tubers, roots, legumes, fruits, and combinations thereof. Starch-based polymers can include glucose monomers joined in an a 1,4 linkage, amylose, amylopectin, and combinations thereof.

Non-limiting examples of native starches can include can include waxy or high amylase varieties of corn, pea, potato, banana, barley, wheat, rice, sago, amaranth, tapioca, arrowroot, canna, sorghum, and combinations thereof.

Non-limiting examples of modified starches can include hydroxypropyl starch, maltodextrin, high amylose starch, and combinations thereof.

Non-limiting examples of fiber polymers can include pectins, fructo-oligosaccharides, inulin, agar, beta-glucans, dextrins, lignin, celluloses, non-starch polysaccharides, reduced starch, polycarbophil, citrus fiber, and combinations thereof.

Non-limiting examples of other naturally sourced polymers can include agar, pullulan, chitin, chitosan, shellac, and combinations thereof.

Non-limiting examples of synthetic polymers can include cellulose derivatives, carbomers, polymethacrylates, other synthetic polymers, and combinations thereof.

Non-limiting examples of cellulose derivatives can include hydroxyethylmethyl cellulose, hydroxylpropylmethyl cellulose, hydroxypropyl cellulose, hydroxypropylethyl cellulose, methylcellulose, hydroxypropyl methylcellulose, and combinations thereof.

Non-limiting examples of carbomers can include carbomer 934, carbomer 934P, carbomer 940, carbomer 94, carbomer 1342, carbomer copolymers, carbomer homopolymers, carbomer interpolymers, and combinations thereof. Some carbomers are available commercially as Carbopol® 934P NF polymer, Carbopol® 971P NF polymer, and Carbopol® 974P NF polymer.

Non-limiting examples of polymethacrylates can include ammonio methacrylate copolymer, basic butylated methacrylate copolymer, methacrylic acid-methyl methacrylate copolymer (1:1), methacrylic acid-ethyl acrylate copolymer (1:1), methacrylic acid-ethyl acrylate copolymer (1:1), methacrylic acid-methyl methacrylate copolymer (1:2), polyacrylate dispersion 30%, methacrylic acid copolymer, amino methacrylate copolymer, ammonio methacrylate copolymer, ammonio methacrylate copolymer dispersion, ethyl acrylate and methyl methacrylate copolymer, and combinations thereof. Some polymethacrylates are available commercially as Eudragit® E 12.5, Eudragit® E 100, Eudragit® E PO, Eudragit® L 12.5 P, Eudragit® L 12.5, Eudragit® L 100, Eudragit® L 100-55, Eudragit® L 30 D-55, Eudragit® S 12.5 P, Eudragit® S 12.5, Eudragit® S 100, Eudragit® FS 30 D, Eudragit® RL 12.5, Eudragit® RL 100, Eudragit® RL PO, Eudragit® RL 30 D, Eudragit® RS 12.5, Eudragit® RS 100, Eudragit® RS PO, Eudragit® RS 30 D, Eudragit® NE 30 D, Eudragit® NE 40 D, Eudragit® NM 30 D, Eastacryl™ 30 D, Kollicoat® MAE 30 DP, Kollicoat® MAE 100 P, Acryl-EZE®, Acryl-EZE® 93 A, and Acryl-EZE® MP.

Non-limiting examples of other synthetic polymers can include polyvinyl alcohol, carboxyvinyl polymers, polyvinyl pyrrolidones, polyethylene oxide, polyoxyethylene, and combinations thereof.

The polymer of the present invention can be selected such that its weight average molecular weight is from about 20,000 Daltons (Da) to about 10,000,000 Da, from about 100,000 Da to about 5,000,000 Da, from about 500,000 Da to about 4,000,000 Da, or from about 1,000,000 Da to about 3,000,000 Da. The weight average molecular weight is computed by summing the weight average molecular weight of each nonwoven web forming material raw material multiplied by their respective relative weight percentages by weight of the total weight of polymers present within the filament.

The polymer can be polyvinyl alcohol with a weight average molecular weight from about 10,000 Da to about 250,000 Da, in another embodiment from about 15,000 Da to about 200,000 Da, and in another embodiment from about 20,000 Da to about 150,000 Da.

The polyvinyl alcohol can have a degree of hydrolysis of from about 60% to 100%, from about 65% to about 85%, less than 85%, from about 70% to about 80%, or from about 65% to about 95%.

The polymer can be selected from the group consisting of alginates, starch-based polymers, native starches, modified starches, and combinations thereof with a weight average molecular weight from about 1,000,000 Da to about 6,000,000 Da, from about 1,500,000 Da to about 5,000,000 Da, or from about 2,000,000 Da to about 4,000,000 Da.

The polymer can be selected from the group consisting of polyvinyl alcohol, pullulan, pectin, corn starch, modified corn starch, hydroxypropyl methylcellulose, and combinations thereof.

The fibrous composition can comprise from about 0.1% to about 50%, from about 5% to about 40%, from about 15% to about 35, from about 20% to about 30%, or from about 15% to about 30% of a polymer, by weight of the fibrous composition.

The nonfibrous composition can comprise from about 0.1% to about 50%, from about 5% to about 40%, from about 15% to about 35, from about 20% to about 30%, or from about 15% to about 30% of a polymer, by weight of the nonfibrous composition or the oral care composition.

Plasticizer

The oral care composition can comprise a plasticizer. Non-limiting examples of plasticizers can include polyols, polycarboxylic acids, polyesters, other suitable plasticizers, and combinations thereof.

Non-limiting examples of polycarboxylic acids can include citric acid, succinic acid, and combinations thereof.

Non-limiting examples of polyesters can include glycerol triacetate, diethyl phthalate, triethyl citrate, tributyl citrate, acetyl triethyl citrate, acetyl tributyl citrate, and combinations thereof.

Non-limiting examples of other suitable plasticizers of the present invention include, but are not limited to, alkyl and allyl phthalates; lactates (e.g., sodium, ammonium and potassium salts); lactic acid; soluble collagen; modified protein; monosodium L-glutamate; proteins and amino acids such as glutamic acid, aspartic acid, and lysine; hydrogen starch hydrolysates; other low molecular weight esters (e.g., esters of C2-C10 alcohols and acids); and any other plasticizer known to one skilled in the art of the food, dietary supplements, and pharmaceutical industries; and combinations thereof.

Polyol

The oral care composition can comprise a polyol. The fibrous composition or the nonfibrous composition can comprise a polyol. The web forming material can comprise a polyol. The foam forming material can comprise a polyol. A polyol is an organic compound with more than one hydroxyl functional groups. The polyol can comprise a sugar alcohol, a non-reducing sugar, a monosaccharide, a disaccharide, a polysaccharide, and/or combinations thereof.

Sugar alcohols are a class of polyols that can be obtained through the hydrogenation of sugar compounds with the formula $(CHOH)_n H_2$, preferably where n=2-6. Suitable sugar alcohols include ethylene glycol, glycerin, erythritol, threitol, arabitol, xylitol, ribitol, mannitol, sorbitol, galactitol, fucitol, iditol, inositol, volemitol, isomalt, maltitol, lactitol, maltomtriitol, maltotetraitol, and/or polyglycitol.

Non-reducing sugars are a class of saccharides that do not generate any compounds containing an aldehyde functional group. Non-reducing sugars are stable in water and do not react with weak oxidizing agents to produce sugar alcohols.

Non-limiting examples of monosaccharides can include glucose, fructose, and combinations thereof.

Non-limiting examples of disaccharides can include sucrose, maltose, lactose, high fructose corn syrup solids, trehalose, cellobiose, gentiobiose, isomaltose, kojibiose, laminaribiose, mannobiose, melibiose, nigerose, rutinose, xylobiose, lactulose and combinations thereof.

Non-limiting examples of trioses can include glyceraldehydes, dihydroxyacetone, and combinations thereof.

Non-limiting examples of tetroses can include erythrose, threose, erythrulose, and combinations thereof.

Non-limiting examples of pentoses can include arabinose, lyxose, ribose, xylose, ribulose, xylulose, and combinations thereof.

Non-limiting examples of hexoses can include allose, altrose, galactose, glucose, gulose, idose, mannose, talose, fructose, psicose, sorbose, tagatose, and combinations thereof.

Non-limiting examples of heptoses can include mannoheptulose, sedoheptulose, and combinations thereof.

Non-limiting examples of octoses can include octolose, 2-keto-3-deoxy-manno-octonate, and combinations thereof. A non-limiting example of nonose can include sialose.

The oral care composition can comprise from about 0.01% to about 50%, from about 0.1% to about 50%, from about 1% to about 40%, from about 2% to about 25%, from about 5% to about 15%, or from about 5% to about 10% of a polyol, by weight of the oral care composition.

Water

The oral care composition can comprise from about 0.01% to about 50%, by weight of the oral care composition of water. The oral care composition can comprise from about 0.01% to about 30%, from about 0.1% to about 25%, from about 0.5% to about 15%, or from about 1% to about 15% of water, by weight of the composition. The water may be added to the formulation directly and/or may come into the composition from the inclusion of other ingredients. Preferably, the water is USP water. Alternatively, the oral care composition can comprise less than about 5%, less than about 1%, less than about 0.5%, or less than about 0.01% water by weight of the total composition. The oral care composition can comprise no added water other than the minimal amount of water in commercial products incorporated into the oral care composition or the water incorporated under ambient conditions.

Abrasive

The oral care composition can comprise about 0.5% to 75% of an abrasive by weight of the oral care composition. The oral care composition can comprise from about 5% to about 60%, from about 10% to about 50%, or from about 15% to about 55%, or combinations thereof, of an abrasive by weight of the composition. The abrasive can be a calcium-containing abrasive, a silica abrasive, a carbonate abrasive, a phosphate abrasive, an alumina abrasive, other suitable abrasives, and/or combinations thereof. Some abrasives may fit into several descriptive categories, such as for example calcium carbonate, which is both a calcium-containing abrasive and a carbonate abrasive.

The calcium-containing abrasive can comprise calcium carbonate, dicalcium phosphate, tricalcium phosphate, calcium orthophosphate, calcium metaphosphate, calcium polyphosphate, calcium hydroxyapatite, and combinations thereof.

The calcium-containing abrasive can comprise calcium carbonate. The calcium-containing abrasive can be selected from the group consisting of fine ground natural chalk, ground calcium carbonate, precipitated calcium carbonate, and combinations thereof.

The carbonate abrasive can comprise sodium carbonate, sodium bicarbonate, calcium carbonate, strontium carbonate, and/or combinations thereof.

The phosphate abrasive can comprise calcium phosphate, sodium hexametaphosphate, dicalcium phosphate, tricalcium phosphate, calcium orthophosphate, calcium metaphosphate, calcium polyphosphate, a polyphosphate, a pyrophosphate, and/or combinations thereof.

The silica abrasive can comprise fused silica, fumed silica, precipitated silica, hydrated silica, and/or combinations thereof.

The alumina abrasive can comprise polycrystalline alumina, calcined alumina, fused alumina, levigated alumina, hydrated alumina, and/or combinations thereof.

Other suitable abrasives include diatomaceous earth, barium sulfate, wollastonite, perlite, polymethylmethacrylate particles, tospearl, and combinations thereof.

The abrasive can be formed within the fibrous composition, added to the surface of the fibrous composition, or included in the nonfibrous composition.

Fluoride Ion Source

The oral care composition may include an effective amount of an anti-caries agent. The oral care composition can comprise a fluoride ion source.

The fluoride ion source may be present in an amount sufficient to give a suitable fluoride ion concentration in the composition according to local laws and regulations, for example the anti-caries monograph at the FDA. The oral care composition can comprise from about 0.0025% to about 20%, from about 0.0025% to about 10%, from about 0.01% to about 5%, or from about 0.0025% to about 2%, by weight of the oral care composition, of the fluoride ion source.

The fluoride ion source can be at an amount suitable to obtain a theoretical fluoride concentration of from about 200 ppm to about 10000 ppm, from about 200 ppm to about 2000 ppm, from about 800 ppm to about 1500 ppm, or from about 1100 ppm to about 1400 ppm as normalized to a unit-dose oral care composition by adding water.

The fluoride ion source can comprise examples of suitable fluoride ion-yielding materials are disclosed in U.S. Pat. Nos. 3,535,421, and 3,678,154. The fluoride ion source can comprise stannous fluoride, sodium fluoride, potassium fluoride, amine fluoride, sodium monofluorophosphate, zinc fluoride, and/or combinations thereof.

The fluoride ion source and the metal ion source can be the same compound, such as for example, stannous fluoride, which can generate tin ions and fluoride ions. Additionally, the fluoride ion source and the tin ion source can be separate compounds, such as when the metal ion source is stannous chloride and the fluoride ion source is sodium monofluorophosphate or sodium fluoride.

The fluoride ion source can be formed within the fibrous composition, added to the surface of the fibrous composition, or included in the nonfibrous composition.

Metal Ion Source

The oral care composition can comprise a metal ion source. Suitable metal ion sources include stannous ion sources, zinc ion sources, copper ion sources, silver ion sources, magnesium ion sources, iron ion sources, sodium ion sources, and manganese (Mn) ion sources, and/or combinations thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions are derived from the metal ion source(s) can be found in the multi-phase oral care composition an effective amount to provide an oral care benefit or other benefits. Stannous, zinc and copper ions have been found to help in the reduction of gingivitis, plaque, sensitivity, and improved breath benefits. An effective amount is defined as from at least about 500 ppm to about 20,000 ppm metal ion of the total composition, preferably from about 2,000 ppm to about 15,000 ppm. More preferably, metal ions are present in an amount from about 3,000 ppm to about 13,000 ppm and even more preferably from about 5,000 ppm to about 10,000 ppm. This is the total amount of metal ions (stannous, zinc, copper and mixtures thereof) that is present in the compositions for delivery to the tooth surface.

Other metal ion sources can include minerals and/or calcium containing compounds, which can lead to remineralization, such as, for example, sodium iodide, potassium iodide, calcium chloride, calcium lactate, calcium phosphate, hydroxyapatite, fluoroapatite, amorphous calcium phosphate, crystalline calcium phosphate, sodium bicarbonate, sodium carbonate, calcium carbonate, oxalic acid, dipotassium oxalate, monosodium monopotassium oxalate, casein phosphopeptides, and/or casein phosphopeptide coated hydroxy apatite.

The metal ion source may comprise a metal salt suitable for generating metal ions in the oral cavity. Suitable metal salts include salts of silver (Ag), magnesium (Mg), iron (Fe), sodium (Na), and manganese (Mn) salts, or combinations thereof. Preferred salts include, without limitation, gluconates, chlorates, citrates, chlorides, fluorides, and nitrates, or combinations thereof.

The oral care composition can comprise at least about 0.005%, from about 0.005% to about 10%, from about 0.01% to about 5%, from about 0.01% to about 2%, or from about 0.1% to about 1% of a metal ion source by weight of the oral care composition. The metal ion source can be formed within the fibrous composition, added to the surface of the fibrous composition, or included in the nonfibrous composition.

Tin Ion Source

Tin ions, such as stannous ions, are used in oral care compositions to deliver benefits such as, for example, enamel care and cavity protection. Suitable tin ion sources include stannous chloride, stannous fluoride, stannous bromide, stannous iodide, stannous acetate, stannous gluconate, stannous oxalate, stannous sulfate, stannous lactate, stannous tartrate stannous carbonate, stannic chloride, stannic fluoride, stannic iodide, stannous citrate, stannic nitrate, stannous peptides, stannous proteins, and stannous phosphate, and combinations thereof. Preferably, the ion source is stannous fluoride, stannous chloride, and/or combinations thereof.

The oral care compositions of the present invention may comprise a tin ion source in the amount ranging from about 0.01% to about 5%, from about 0.05% to about 4%, from about 0.01% to about 10%, or from about 0.075% to about 3%. The tin ion source can be formed within the fibrous composition, added to the surface of the fibrous composition, or included in the nonfibrous composition.

Zinc Ion Source

The oral care composition may comprise from about 0.01% to about 5%, from about 0.2% to about 2%, or from about 0.01% to about 10%, by weight of the oral care composition, of a zinc ion source. The zinc ion source can be selected from the group consisting of zinc citrate, zinc chloride, zinc sulfate, zinc gluconate, zinc lactate, zinc phosphate, zinc arginine, zinc fluoride, zinc iodide, zinc carbonate, and combinations thereof. More preferably, the zinc ion source is selected from zinc citrate, zinc gluconate, zinc lactate, and combinations thereof. Insoluble or sparingly soluble zinc compounds, such as zinc oxide or zinc carbonate, can be used as the zinc ion source. Zinc ion sources can be soluble zinc sources such as zinc chloride or zinc sulfate. Additionally, zinc ion sources can be those where the zinc is already combined with a suitable chelating agent in the form of a salt or other complex, such as zinc citrate, zinc gluconate, zinc lactate and zinc glycinate. Other examples of zinc ion sources are zinc citrate, zinc gluconate, zinc lactate and mixtures thereof.

When insoluble and soluble zinc compounds are both present in the zinc ion source, the soluble zinc compound can be present at least about 50%, by weight of the total zinc ion source. The oral care compositions of the present invention may optionally also include other antibacterial agents, preferably present in an amount of from about 0.035% or more, from about 0.05% to about 2%, from about 0.1% to about 1%, by weight of the oral care composition. Examples of these other anti-bacterial agents may include non-cationic anti-bacterial agents such as, for example, halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilidies. Other useful anti-bacterial agents are enzymes, including endoglycosidase, papain, dextranase, mutanase, and combinations thereof. In another example, the other anti-bacterial agent can include triclosan (5-chloro-2-(2,4-dichlorophenoxy)phenol).

The zinc ion source can be formed within the fibrous composition, added to the surface of the fibrous composition, or included in the nonfibrous composition.

Copper Ion Source

The oral care composition can comprise from about 0.01% to about 5%, from about 0.2% to about 2%, or from about 0.01% to about 10%, by weight of the oral care composition, of a copper ion source. The copper ion source can be selected from the group consisting of copper gluconate, copper citrate, copper fluoride, copper iodide, copper bromide, copper peptides, copper sulfate, copper arginine, copper carbonate, and combinations thereof. Copper salts can be in any possible oxidation state, including, for example, copper(I) or copper(II) salts. The copper ion source can be formed within the fibrous composition, added to the surface of the fibrous composition, or included in the nonfibrous composition.

Calcium Ion Source

The oral care composition can comprise a calcium ion source. The calcium ion source can comprise a calcium salt, such as, for example, calcium chloride, and/or a calcium-containing abrasive, as described herein.

The calcium compound can comprise any suitable soluble calcium salt, such as for example, calcium chloride, calcium carbonate, calcium bicarbonate, calcium hydroxide, calcium lactate, calcium citrate, calcium phosphate, and combinations thereof.

The oral care composition can comprise from about 0.01% to about 10%, from about 1% to about 50%, from about 10% to about 50%, or from about 1% to about 30%, by weight of the oral care composition of a calcium ion source.

Surfactants

The oral care composition can comprise one or more surfactants. The fibrous composition can comprise one or more surfactants. The nonfibrous composition can comprise one or more surfactants. The one or more surfactants may be selected from anionic, nonionic, amphoteric, zwitterionic, cationic surfactants, or combinations thereof.

The oral care composition may include one or more surfactants at a level of from about 0.01% to about 20%, from about 1% to about 15%, from about 0.1% to about 15%, from about 5% to about 15%, or greater than about 5%%, by weight of the composition.

Suitable anionic surfactants include, for example, the water soluble salts of alkyl sulfates having from 8 to 20 carbon atoms in the alkyl radical and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzene sulfonate. Combinations of anionic surfactants can also be employed.

Another suitable class of anionic surfactants are alkyl phosphates. The surface active organophosphate agents can have a strong affinity for enamel surface and have sufficient surface binding propensity to desorb pellicle proteins and remain affixed to enamel surfaces. Suitable examples of organophosphate compounds include mono-, di- or triesters represented by the general structure below wherein $Z_1$, $Z_2$, or $Z_3$ may be identical or different with at least one being an organic moiety. $Z_1$, $Z_2$, or $Z_3$ can be selected from linear or branched, alkyl or alkenyl group of from 1 to 22 carbon atoms, optionally substituted by one or more phosphate groups; alkoxylated alkyl or alkenyl, (poly)saccharide, polyol or polyether group.

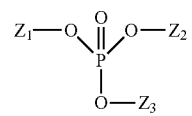

Some other agents include alkyl or alkenyl phosphate esters represented by the following structure:

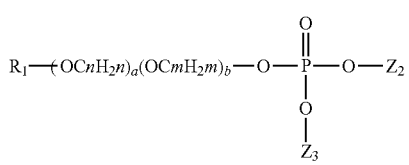

wherein $R_1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z and Z may be identical or different, each represents hydrogen, alkali metal, ammonium, protonated alkyl amine or protonated functional alkylamine, such as analkanolamine, or a R—(OCH2)(OCH)— group. Examples of suitable agents include alkyl and alkyl (poly) alkoxy phosphates such as lauryl phosphate; PPGS ceteareth-10 phosphate; laureth-1 phosphate; laureth-3 phosphate; laureth-9 phosphate; trilaureth-4 phosphate; $C_{12-18}$ PEG 9 phosphate: and sodium dilaureth-10 phosphate. The alkyl phosphate can be polymeric. Examples of polymeric alkyl phosphates include those containing repeating alkoxy groups as the polymeric portion, in particular 3 or more ethoxy, propoxy isopropoxy or butoxy groups.

Other suitable surfactants are sarcosinates, isethionates and taurates, especially their alkali metal or ammonium salts. Examples include: lauroyl sarcosinate, myristoyl sarcosinate, palmitoyl sarcosinate, stearoyl sarcosinate oleoyl sarcosinate, or combinations thereof.

Zwitterionic or amphoteric Surfactants useful herein include derivatives of aliphatic quaternary ammonium, phosphonium, and Sulfonium compounds, in which the aliphatic radicals can be straight chain or branched, and one of the aliphatic substituents contains from 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577. Typical alkyl dimethyl betaines include decyl betaine or 2-(N-decyl-N,N-dimethylammonio) acetate, coco-betaine or 2-(N-coco-N,N-dimethyl ammonio)acetate, myristyl betaine, palmityl betaine, lauryl betaine, cetyl betaine, cetyl betaine, stearyl betaine, etc. The amidobetaines can be exemplified by cocoamidoethyl betaine, cocoamidopropyl betaine (CADB), and lauramidopropyl betaine.

Cationic surfactants useful in the present invention include, for example, derivatives of quaternary ammonium compounds having one long alkyl chain containing from 8 to 18 carbon atoms such as lauryl trimethylammonium chloride; cetyl pyridinium chloride; cetyl trimethyl-ammonium bromide; cetyl pyridinium fluoride or combinations thereof.

Nonionic surfactants that can be used in the compositions of the present invention include, for example, compounds produced by the condensation of alkylene oxide groups (hydrophilic in nature) with an organic hydrophobic compound which may be aliphatic or alkylaromatic in nature. Examples of suitable nonionic surfactants can include the Pluronics® which are poloxamers, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and combinations of such materials.

The one or more surfactants can also include one or more natural surfactants. Natural surfactants can include surfactants that are derived from natural products and/or surfactants that are minimally or not processed. Natural surfactants can include hydrogenated, non-hydrogenated, or partially hydrogenated vegetable oils, olus oil, *Passiflora incarnata* oil, candelilla cera, coco-caprylate, caprate, dicaprylyl ether, lauryl alcohol, myristyl myristate, dicaprylyl ether, caprylic acid, caprylic ester, octyl decanoate, octyl octanoate, undecane, tridecane, decyl oleate, oleic acid decylester, cetyl palmitate, stearic acid, palmitic acid, glyceryl stearate, hydrogenated, non-hydrogenated, or partially hydrogenated vegetable glycerides, Polyglyceryl-2 dipolyhydroxystearate, cetearyl alcohol, sucrose polystearate, glycerin, octadodecanol, hydrolyzed, partially hydrolyzed, or non-hydrolyzed vegetable protein, hydrolyzed, partially hydrolyzed, or non-hydrolyzed wheat protein hydrolysate, polyglyceryl-3 diisostearate, glyceryl oleate, myristyl alcohol, cetyl alcohol, sodium cetearyl sulfate, cetearyl alcohol, glyceryl laurate, capric triglyceride, coco-glycerides, lecithin, dicaprylyl ether, xanthan gum, sodium coco-sulfate, ammonium lauryl sulfate, sodium cocoyl sulfate, sodium cocoyl glutamate, polyalkylglucosides, such as decyl glucoside, cetearyl glucoside, cetyl stearyl polyglucoside, coco-glucoside, and lauryl glucoside, and/or combinations thereof. Natural surfactants can include any of the Natrue ingredients marketed by BASF, such as, for example, CegeSoft®, Cetiol®, Cutina®, Dehymuls®, Emulgade®, Emulgin®, Eutanol®, Gluadin®, Lameform®, LameSoft®, Lanette®, Monomuls®, Myritol®, Plantacare®, Plantaquat®, Platasil®, Rheocare®, Sulfopon®, Texapon®, and/or combinations thereof.

The surfactant can be formed within the fibrous composition, added to the surface of the fibrous composition, and/or included in the nonfibrous composition. The surfactant formed within the fibrous composition can be at a level from about 10% to about 50%, from about 20% to about 40%, from about 25% to about 40%, or from about 30% to about 40% by weight of the fibrous composition.

The oral care composition can comprise one or more surfactants. The oral care composition can comprise an anionic surfactant, a cationic surfactant, a nonionic surfactant, and/or a zwitterionic surfactant.

The oral care composition can comprise from about 0.1% to about 10%, from about 0.1% to about 8%, from about 5% to about 8%, from about 4% to about 9%, or from about 3% to about 10% of an anionic surfactant, cationic surfactant, and/or nonionic surfactant by weight of the composition.

The oral care composition can comprise from about 0.01% to about 20%, from about 0.01% to about 10%, from about 0.1% to about 1%, from about 0.01% to about 1%, from about 0.01% to about 0.5%, or from about 0.1% to about 0.2% of a zwitterionic surfactant by weight of the composition.

PEG

The oral care composition may comprise polyethylene glycol (PEG), of various weight percentages of the composition as well as various ranges of average molecular weights. The compositions can have from about 0.1% to about 40%, from about 1% to about 35%, from about 5% to about 30%, from about 15% to about 25%, from about 1% to about 40%, from about 10% to about 30%, from about 15% to about 20%, from about 0.1% to about 30%, or from about 15% to about 30% of PEG by weight of the composition. The PEG can have a range of average molecular weight from about 100 Daltons to about 1600 Daltons, from about 200 to about 1000, from about 400 to about 800, from about 500 to about 700 Daltons, or combinations thereof. PEG is a water soluble linear polymer formed by the addition reaction of ethylene oxide to an ethylene glycol equivalent having the general formula: $H-(OCH_2CH_2)_n-OH$. One supplier of PEG is Dow Chemical Company under the brandname of CARBOWAX™.

PEG can be formed within the fibrous composition, added to the surface of the fibrous composition, or included in the nonfibrous composition. PEG included in the nonfibrous composition can be at a level from about 10% to about 50%, from about 15% to about 40%, from about 5% to about 35%, or from about 15% to about 30% by weight of the nonfibrous composition. The PEG, when used as a solvent for the nonfibrous composition, can be anhydrous to prevent reactivity between components dispersed or dissolved within the PEG.

Polyphosphates

The oral care composition can comprise a polyphosphate source. A polyphosphate source can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. The polyphosphate source can also include alkali earth metal polyphosphate salts, and specifically calcium polyphosphate salts, such as calcium pyrophosphate, due to the ability to separate calcium ions from other reactive components, such as fluoride ion sources.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The oral care composition can comprise from about 0.01% to about 15%, from about 0.1 to about 10%, from about 0.5% to about 5%, from about 1 to about 20%, or about 10% or less, by weight of the oral care composition, of the polyphosphate source.

Extensional Aid

The oral care composition can comprise an extensional aid. Non-limiting examples of extensional aids can include polymers, other extensional aids, and combinations thereof.

The extensional aids can have a weight average molecular weight of at least about 500,000 Da. The weight average molecular weight of the extensional aid can be from about 500,000 to about 25,000,000, from about 800,000 to about 22,000,000, from about 1,000,000 to about 20,000,000, or from about 2,000,000 to about 15,000,000. The high molecular weight extensional aids are preferred in some embodiments of the invention due to the ability to increase extensional melt viscosity and reducing melt fracture.

The extensional aid, when used in meltblowing, can be added to the composition of the present invention in an amount effective to visibly reduce the melt fracture and capillary breakage of filaments during the spinning process such that substantially continuous filaments having relatively consistent diameter can be melt spun. Regardless of the process employed to produce filaments, the extensional aids, when used, can be present from about 0.001% to about 10%, by weight on a dry filament basis, from about 0.005 to about 5%, by weight on a dry filament basis, from about 0.01 to about 1%, by weight on a dry filament basis, or from about 0.05% to about 0.5%, by weight on a dry filament basis.

Non-limiting examples of polymers that can optionally be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include carboxyl modified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Aesthetic Agents

The oral care composition can optionally comprise one or more aesthetic agents. The one or more aesthetic agents can be selected from the group consisting of flavors, colorants, sensates, sweeteners, salivation agents, and combinations thereof. All aesthetic agents can be present from about 0.001% to about 60%, by weight of the oral care composition, from about 0.005% to about 50%, by weight of the oral care composition, about 0.05% to about 40%, by weight of the oral care composition, or from about 0.1% to about 35%, by weight of the oral care composition.

Aesthetic agents can be formed within the fibrous composition, added to the surface of the fibrous composition, or included in the nonfibrous composition.

Flavors

The oral care composition can optionally include one or more flavors. Non-limiting examples of flavors that can be used in the present invention can include natural flavoring agents, artificial flavoring agents, artificial extracts, natural extracts and combination thereof. Non-limiting examples of flavors can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, mouth cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, adipic acid, citral, denatonium benzoate, ethyl acetate, ethyl lactate, ethyl maltol, ethylcellulose, fumaric acid, leucine, malic acid, menthol, methionine, monosodium glutamate, sodium acetate, sodium lactate, tartaric acid, thymol, and combinations thereof.

Flavors can be protected in an encapsulate or as a flavor crystal. The encapsulated flavor can have a controlled or delayed release once the encapsulated flavor reaches the oral cavity. The encapsulate can comprise a shell and a core. The flavor can be in the core of the encapsulate. The flavor can be encapsulated by any suitable means, such as spray drying or extrusion. Encapsulated flavors can be added to the surface of the fibrous composition, formed within the fibrous composition, or included in the nonfibrous composition.

Flavors can be present from about 0.05% to about 25%, by weight of the oral care composition, from about 0.01% to about 15%, by weight of the oral care composition, from about 0.2% to about 10%, by weight of the oral care composition, or from about 0.1% to about 5%, by weight of the oral care composition.

Flavors can be formed within the fibrous composition, added to the surface of the fibrous composition, or included in the nonfibrous composition.

Colorants

The oral care composition can optionally include one or more colorants. The colorants can provide a visual signal when the oral care composition is exposed to conditions of intended use. Non-limiting examples colorants that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. Colorants can be present from about 0.05% to about 2%, by weight of the oral care composition, from about 0.01% to about 2%, by weight of the oral care composition, or from about 0.02% to about 1.5%, by weight of the oral care composition.

Colorants can be formed within the fibrous composition, added to the surface of the fibrous composition, or included in the nonfibrous composition.

Sensates

The oral care composition can optionally include one or more sensates. Non-limiting examples of sensates can include cooling sensates, warming sensates, tingling sensates, and combinations thereof. Sensates are useful to deliver signals to the user.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-,ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol (sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P®" by Takasago International., cis & trans p-Menthane-3,8-diols (PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl (2-hydroxyethoxy)acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthane glycerin acetal, Peppermint oil, Givaudan 180, L-Monomenthyl succinate, L-monomenthyl glutarate, 3-1-menthoxypropane-1,2-diol—(Coolact 10), 2-1-menthoxyethanol (Cooltact 5), TK10 Coolact (3-1-Menthoxy propane-1,2-diol), Evercool 180 (N-p-benzeneacetonitrile-menthane carboxamide), and combinations thereof. Cooling sensates can be present from about 0.005% to about 10%, by weight of the oral care composition, from about 0.05% to about 7%, by weight of the oral care composition, or from about 0.01% to about 5%, by weight of the oral care composition.

Non-limiting examples of warming sensates can include TK 1000, TK 1 MM, Heatenol—Sensient Flavors, Optaheat—Symrise Flavors, Cinnamon, Polyethylene glycol, Capsicum, Capsaicin, Curry, FSI Flavors, Isobutavan, Ethanol, Glycerin, Nonivamide 60162807, Hotact VEE, Hotact 1MM, piperine, optaheat 295 832, optaheat 204 656, optaheat 200 349, and combinations thereof. Warming sensates can be present from about 0.005% to about 60%, by weight on a dry filament basis, from about 0.05% to about 50%, by weight on a dry filament basis, or from about 0.01% to about 40%, by weight on a dry filament basis. Warming sensates can be present from about 0.005% to about 10%, by weight of the oral care composition, from about 0.05% to about 7%, by weight of the oral care composition, or from about 0.01% to about 5%, by weight of the oral care composition. Non-limiting examples of tingling sensates can include sichuan pepper, hydroxy alpha sanshool, citric acid, Jambu extracts, spilanthol, and combinations thereof. Tingling sensates can be present from about 0.005% to about 10%, by weight on a dry filament basis or the oral care composition, from about 0.01% to about 7%, by weight on a dry filament basis or the oral care composition, or from about 0.015% to about 6%, by weight on a dry filament basis or the oral care composition.

Sensates can be formed within the fibrous composition, added to the surface of the fibrous composition, or included in the nonfibrous composition.

Sweeteners

The oral care composition can optionally include one or more sweeteners. Sweeteners can be natural or artificial. Non-limiting examples of sweeteners can include nutritive sweeteners, sugar alcohols, synthetic sweeteners, high intensity natural sweeteners, and combinations thereof. All sweeteners can be present from about 0.05% to about 60%, by weight of the oral care composition, from about 0.1% to about 50%, by weight of the oral care composition, or from about 1% to about 10%, by weight of the oral care composition.

Non-limiting examples of nutritive sweeteners can include sucrose, dextrose, glucose, fructose, lactose, tagatose, maltose, trehalose, and combinations thereof. Nutritive sweeteners can be present from about 0.1% to about 60%, by weight of the oral care composition, from about 1% to about 50%, by weight of the oral care composition, or from about 0.1% to about 10%, by weight of the oral care composition.

Non-limiting examples of sugar alcohols can include xylitol, sorbitol, mannitol, maltitol, lactitol, isomalt, erythritol, and combinations thereof. Sugar alcohols can be present from about 0.1% to about 60%, by weight of the oral care composition, from about 0.11% to about 50%, by weight of the oral care composition, or from about 0.1% to about 10%, by weight of the oral care composition.

Non-limiting examples of synthetic sweeteners can include aspartame, acesulfame potassium, alitame, sodium saccharin, sucralose, neotame, cyclamate, and combinations thereof. Synthetic sweeteners can be present from about 0.05% to about 10% by weight of the oral care composition, from about 0.1% to about 5%, by weight of the oral care composition, or from about 0.25% to about 4%, by weight of the oral care composition.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof. High intensity natural sweeteners can be present from about 0.05% to about 10% by weight of the oral care composition, from about 0.1% to about 5%, by weight of the oral care composition, or from about 0.25% to about 4%, by weight of the oral care composition.

Sweeteners can be formed within the nonwoven web, added to the surface of the nonwoven web, or included in the nonfibrous composition.

Salivation Agents

The oral care composition can optionally include one or more salivation agents. Non-limiting examples of salivation agents include formula (I):

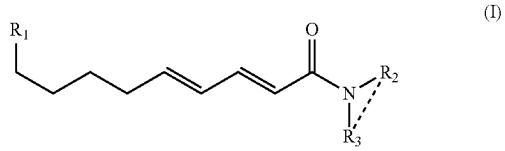
(I)

wherein $R_1$ represents C1-C2 n-alkyl; $R_2$ is 2-methyl-1-propyl and $R_3$ is hydrogen, or $R_2$ and $R_3$ taken together is a moiety (designated by the dashed lines) having the formula $-(CH_2)_n-$ wherein n is 4 or 5, and combinations thereof.

The salivating agent can comprise a material wherein $R_2$ is 2-methyl-1-propyl and $R_3$ is hydrogen or the salivating agent can comprise a material wherein $R_1$ is C1 n-alkyl, $R_2$ is 2-methyl-1-propyl and $R_3$ is hydrogen. The salivating agent can comprise trans-pellitorin, a chemical having a structure according to formula (II):

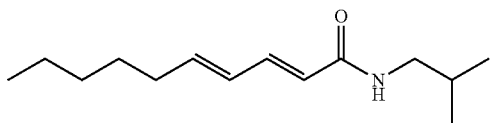
(II)

The salivation agent can include sodium bicarbonate, sodium chloride, trans pelitorin, pilocarpine, citrate, and combinations thereof. Salivation agents can be present from about 1% to about 60%, from about 1% to about 50%, or from about 1% to about 40%, by weight of the oral care composition. Additionally, salivation agents can be present from about 0.005% to about 10%, by weight of the oral care composition, from about 0.01% to about 7%, by weight of the oral care composition, or from about 0.015% to about 6%, by weight of the oral care composition.

Salivation agents can be formed within the fibrous composition, added to the surface of the fibrous composition, or included in the nonfibrous composition.

Thickening Agent

The oral care compositions herein may include one or more thickening agents. A thickening agent may be used in an amount from about 0.01% to about 15%, or from about 0.1% to about 10%, or from about 0.1% to about 5%, by weight of the oral care composition. Non-limiting examples may include those described in US 2008/0081023 A1 at paragraphs 134 to 137, and the references cited therein.

The oral care composition can comprise a linear sulfated polysaccharide as a thickening agent. Carrageenans or carrageenans are one example of a linear sulfated polysaccharide. Generally, carrageenans can vary based upon the degree of sulfation that includes: Kappa-carrageenan, Iota-carrageenan, and Lambda-carrageenan. Combinations of carrageenans can be used. The oral care composition can contain from about 0.1% to about 3%, of a linear sulfated polysaccharides by weight of the oral care composition, from about 0.5% to about 2%, from about 0.6% to about 1.8%, or combinations thereof.

The oral care composition can comprise a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). The oral care composition can include from about 0.5% to about 5% by weight of the oral care composition of a silica agent, preferably from about 1% to about 4%, alternatively from about 1.5% to about 3.5%, alternatively from about 2% to about 3%, alternatively from about 2% to about 5% alternatively from about 1% to about 3%, alternatively combinations thereof.

The thickening agent can comprise a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9 M3SF Aqualon™ TM9A; Aqualon™ TM12A). The thickening agent can contain from about 0.1% to about 3% of a CMC by weight of the oral care composition, preferably from about 0.5% to about 2%, alternatively from about 0.6% to about 1.8%, alternatively combinations thereof.

Thickening agents can be formed within the fibrous composition, added to the surface of the fibrous composition, or included in the nonfibrous composition.

Chelants

The oral care compositions of the present invention can comprise one or more chelants, also known as chelating agents. The term "chelant", as used herein means a bi- or multidentate ligand having at least two groups capable of binding to metal ions and preferably other divalent or polyvalent metal ions and which, at least as part of a chelant mixture, is capable of solubilizing tin ions or other optional metal ions within the oral care composition. Groups capable of binding to metal ions include carboxyl, hydroxyl, and amine groups.

Suitable chelants herein include C2-C6 dicarboxylic and tricarboxylic acids, such as succinic acid, malic acid, tartaric acid and citric acid; C3-C6 monocarboxylic acids substituted with hydroxyl, such as gluconic acid; picolinic acid; amino acids such as glycine; salts thereof and mixtures thereof. The chelants can also be a polymer or copolymer in which the chelating ligands are on the same or adjacent monomer Preferred chelant polymers are polyacids selected from the group consisting of a homopolymer of a monomer, a co-polymer of two or more different monomers, and a combination thereof wherein the monomer or at least one of the two or more different monomers is selected from the group consisting of acrylic acid, methacrylic acid, itaconic acid, maleic acid, glutaconic acid, aconitic acid, citraconic acid, mesaconic acid, fumaric acid and tiglic acid. Particularly preferred is a methylvinylether/maleic acid (PVM/MA) copolymer. Other useful chelants include polyphosphates, as discussed herein.

Preferred organic acid chelants herein comprise citrate, malate, tatirate, gluconate, succinate, lactate, malonate, maleate, and mixtures thereof, whether added in their free acid or salt forms.

The oral care compositions of the present invention can have low levels of chelants because metals ions can require less stabilization if introduced in a fibrous composition, a nonfibrous composition, or physically separated from other reactive components of the oral care composition, which can be added in a separate web layer or in the nonfibrous composition. The oral care composition can have less than about 5%, less than about 1%, less than about 0.5%, less than 0.1%, less than about 0.01%, or 0% of chelants, by weight of the oral care composition. Chelants can be formed within the fibrous composition, added to the surface of the fibrous composition, or included in the nonfibrous composition.

Whitening Agents

The oral care composition may further comprise from about 0.1% to about 10%, from about 0.2% to about 5%, from about 1% to about 5%, or from about 1% to about 15%, by weight of the total oral care composition of a whitening agent. The whitening agent can be a compound suitable for whitening at least one tooth in the oral cavity. The whitening agent may include peroxides, metal chlorites, perborates, percarbonates, peroxyacids, persulfates, and combinations thereof. Suitable peroxides include solid peroxides, urea peroxide, calcium peroxide, benzoyl peroxide, sodium peroxide, barium peroxide, inorganic peroxides, hydroperoxides, organic peroxides, and mixtures thereof. Suitable metal chlorites include calcium chlorite, barium chlorite, magnesium chlorite, lithium chlorite, sodium chlorite, and potassium chlorite. Other suitable whitening agents include sodium persulfate, potassium persulfate, peroxydone, 6-phthalimido peroxy hexanoic acid, Pthalamidoperoxycaproic acid, or mixtures thereof.

Whitening agents can be reactive with other components of oral care compositions, thus, can be separated from other components using the assembly design described herein. Whitening agents can be formed within the fibrous composition, added to the surface of the fibrous composition, or included in the nonfibrous composition.

Bioactive Materials

The oral care composition can also include bioactive materials suitable for the remineralization of a tooth. Suitable bioactive materials include bioactive glasses, Novamin™, Recaldent™ hydroxyapatite, amino acids, such as, for example, arginine, citrulline, glycine, lysine, or histidine, or combinations thereof. Other suitable bioactive materials include any calcium phosphate compound. Other suitable bioactive materials include compounds comprising a calcium source and a phosphate source.

Bioactive glasses are comprising calcium and/or phosphate which can be present in a proportion that is similar to hydroxyapatite. These glasses can bond to the tissue and are biocompatible. Bioactive glasses can include a phosphopeptide, a calcium source, phosphate source, a silica source, a sodium source, and/or combinations thereof.

The oral care composition can comprise from about 0.01% to about 20%, from about 0.1% to about 10%, or from about 1% to about 10% of a bioactive material by weight of the oral care composition.

Bioactive materials can be formed within the fibrous composition, added to the surface of the fibrous composition, or included in the nonfibrous composition.

Nonfibrous Compositions

The components described herein can optionally be present, at least partially, as a nonfibrous composition. The nonfibrous composition can be between two or more web layers, folded inside at least one web layer, rolled inside at least web layer, or wrapped in at least one web layer. At least a portion of the nonfibrous composition can contact the surface of a fibrous composition. The nonfibrous composition can be liquid, solid, aqueous, and/or combinations thereof.

The nonfibrous composition may comprise an oral care active, aesthetic agent, abrasive, fluoride ion source, web forming material, metal ion source, polyphosphate, chelant, anti-calculus agent, thickening agent, polymer, surfactant, bioactive material and/or combinations thereof.

The nonfibrous composition can be from about 10% to about 90%, from about 20% to about 85%, from about 30% to about 80%, from about 40% to about 75%, from about 50% to about 80%, from about 50% to about 90%, or from about 60% to about 80% by weight of the oral care composition.

The density of the nonfibrous composition can be from about 0.05 $g/cm^3$ to about 5 $g/cm^3$, from about 0.75 $g/cm^3$ to about 1.9 $g/cm^3$, from about 1 $g/cm^3$ to about 1.75 $g/cm^3$, or from about 1.4 $g/cm^3$ to about 1.8 $g/cm^3$.

Coating Composition

The components described herein can optionally be present, at least partially, as a coating composition. The coating composition can be applied to the fibrous composition, web, or the oral care composition. The coating composition at least partially covers or covers an outer surface of the fibrous composition or the web. The coating composition can cover an outer surface of the oral care composition putting the coating composition in position to immediately contact the target surface (e.g. saliva in the mouth) during use for the release of the oral care active(s) and/or aesthetic agent(s).

The coating composition of the present invention may comprise one or more oral care actives as defined herein. The coating composition of the present invention may comprise one or more aesthetic agents as defined herein.

The fibrous composition, web, or oral care composition may comprise one or more oral care actives which can be the same or different from the oral care active present in the coating composition. The fibrous composition, web, or oral care composition can comprise a delayed delivery, an extended delivery oral care active, and/or a targeted delivery oral care active and the coating composition comprises an immediate delivery oral care active. The fibrous composition, web, or oral care composition can comprise one or more aesthetic agents which can be the same or different from the aesthetic agent in the coating composition.

The coating composition can also be entrapped within the fibrous composition or the web. Thus, the particles of the coating composition can fit within the void between the fibers or filaments when formed into a web using any suitable means.

Releasable Components

Oral care actives, aesthetic agents, or other components in the oral care composition can be designed to be releasable upon a suitable triggering condition. The releasable components can be releasable on the same or a different triggering condition. For example, a flavor encapsulate can be releasable upon a shear rate associated with a user brushing at least one tooth. A fluoride ion source can be releasable upon contact with water. This can allow for oral care actives or aesthetic agents to be released at a designable time. For example, a flavor can be released 1 seconds after brushing while a colorant can be releasable after a user has brushed for two minutes to indicate a suitable brushing time has passed. Aesthetic agents or oral care actives can be delivered sequentially or simultaneous with other aesthetic agents or oral care actives.

Graphics

Graphics can be printed directly on the oral care compositions. Suitable graphics include graphics to match flavors, graphics of sports teams logos or names, graphics to match directions for use, such as use at a particular time of day, after consuming a certain food or drink, or the type of brush to use, marketing material, colors, designs, logos, graphics depicting fictional and nonfictional characters, graphics tied to a consumer benefit, flags, phrases, catch phrases, motivational quotes, branding material, company information, ingredient lists, animals, or other suitable graphics to convey information directly on the oral care compositions. Graphics can be printed on each side of the oral care composition. Graphics can be the same or different on each side of the oral care composition.

Dissolution Time

The oral care compositions of the present invention can be described by their dissolution times. The oral care compositions of the present invention dissolve much quicker than a comparable paste dentifrice. Oral care compositions comprising a fibrous composition of the present invention can have a total dissolution time according to the dissolution method, as described herein, of less about 1000 seconds, less than about 750 seconds, less than about 500 seconds, less than about 250 seconds, from about 50 seconds to about 250 seconds, or from about 50 seconds to about 500 seconds per dose of oral care composition. Foam compositions of the present invention can have a total dissolution time according to the dissolution method described herein of less than about 50 seconds, less than about 30 seconds, or less than about 20 seconds per dose of the foam composition. Comparable dentifrice paste formulations have dissolution times of greater than 1000 seconds which is not suitable for a unit-dose oral care composition that needs to dissolve upon contact with moisture in the oral cavity.

Fluoride Uptake

The oral care compositions, as described herein, can be described according its average fluoride uptake by HAP dissolution. The oral care compositions of the present invention have a higher average F uptake despite also comprising components that are typically avoided or carefully avoided due to reactivity with fluoride ions. For example, the oral care compositions can have an average fluoride uptake of at least 1000 ppm, at least 1500 ppm, or at least 2000 ppm despite comprising a fluoride ion source and a calcium ion source, which can react to form precipitated calcium fluoride prior to use by a consumer. The oral care compositions, as described herein, physically separate the fluoride ion source from the calcium ion source in a different nonwoven web layers, in separate portions, in separate compositions of the oral care compositions, or in a soluble solid phase. The physical separation of these components have been previously difficult to achieve. Unit-dose oral care compositions, such as pouches, solid foams, or soluble fibrous compositions, provide the chassis that can physically separate fluoride ions from calcium ions during storage, but also allows them to be combinable upon dissolution and/or disintegration in the oral cavity.

Tin Ion Uptake

The oral care compositions, as described herein, can be described according its average tin ion uptake by HAP dissolution. The oral care compositions of the present invention have a higher average Sn uptake despite also comprising components that are typically avoided or carefully formulated due to reactivity with tin ions. For example, the oral care compositions can have an average tin ion uptake of at least 5000 ppm, at least 10000 ppm, or at least 20000 ppm despite comprising a tin ion source and a polyphosphate, silica abrasive, etc., which can react to form tin complexes that low the tin ion availability prior to use by a consumer. The oral care compositions, as described herein, physically separate the metal ion source from polyphosphates, silica abrasives, or other chelants in a different nonwoven web layers, in separate portions, in separate compositions of the oral care compositions, or in a soluble solid phase. The physical separation of these components have been previously difficult to achieve. Unit-dose oral care compositions, such as pouches, solid foams, or soluble fibrous compositions, provide the chassis that can physically separate metal ions from other reactive components during storage, but also allows them to be combinable upon dissolution and/or disintegration in the oral cavity.

Morphology

The oral care composition, as described herein, can be described by its morphology, which is unique relative to other oral care compositions, such as dentifrice pastes and/or mouth rinses. For example, the unit-dose oral care composition comprising a fibrous composition can be a nonwoven web of fiber and/or filaments. The unit-dose oral care composition comprising a solid soluble foam composition can have voids within a solid foam network connected by struts. The solid soluble foam compositions can have a mean void volume percentage, or the ratio between void-space to the total space occupied by the foam, of at least about 75%, at least about 85% or at least about 88%. In contrast, the fibrous compositions can have a mean void volume of from about 15% to about 75%, from about 15% to about 70%, from about 30% to about 75%, or from about 35% to about 70%. Dentifrice pastes and/or mouth rinses would have mean void volume percentages of less than 15% prior to use by a consumer.

Solid soluble foam compositions can have an average pore size of greater than about 0.1 mm, greater than about 0.2 mm, or greater than about 0.3 mm. In contrast, the fibrous compositions can have an average pore size of from about 0.001 mm to about 0.1 mm, from about 0.01 mm to about 0.05 mm, or from about 0.01 mm to about 0.1 mm. Dentifrice pastes and/or mouth rinses would not be expected to have pores until use by a consumer since they are liquids and/or pastes.

Solid soluble foam compositions can have a surface area of from about 50 $mm^{-1}$ to about 150 $mm^{-1}$, from about 75 $mm^{-1}$ to about 160 $mm^{-1}$, or from about 100 $mm^{-1}$ to about 150 mm$^{-1}$. In contrast, the surface of fibrous compositions can be at least about 150 mm$^{-1}$, at least about 200 mm$^{-1}$, or at least about 250 mm$^{-1}$.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Unit-Dose Dentifrice Preparation

Fibrous Unit-Dose Compositions

Fibrous unit-dose oral care compositions were assembled from a fibrous composition and a nonfibrous composition. The fibrous composition was made by first adding USP water to a batch mixing tank. The target amount of water is 60 wt % including the water introduced with any aqueous components, thus, the actual amount of the components added varies based on the batch size and the target composition. Next, the target amount of xylitol or sorbitol was added to the batch mixing tank while mixing at 60 rpm. The target amount of polyvinyl alcohol was added to the batch mixing tank. The batch mixing tank was heated to 80° C. The mixture was heated and stirred for 2 hours at 80° C. and 120 rpm.

The target amount of sodium lauryl sulfate and cocamidopropyl betaine were added in succession as aqueous solutions. Next, sucralose was then added to the mixture. Finally, the fluoride ion source and/or chelant was then added, if desired. The fibrous composition melt was allowed to degas over night while being stirred at 70° C.

The fibrous composition melt was allowed to cool to 40° C. and the fibrous composition melt was spun into filaments and/or fibers. The fibrous composition melt was transferred from the batch mixing tank to the fiber spinning die. Fibers and/or filaments were extruded via a Biax-fiberfilm multi-row capillary die at 60° C. The fibers and/or filaments were attenuated and dried with hot air to have less than 5% moisture. The fibers and/or filaments were collected on a belt as the fibrous composition.

The nonfibrous composition was synthesized by adding the components listed in TABLE 1 to PEG 600 with mechanical mixing to create a slurry.

The fibrous unit-dose compositions were assembled by placing a first strip of the fibrous composition onto a die plate. Cavities in the fibrous composition were made by applying force within each die well. The nonfibrous composition was applied to the interior of the cavity with a dropper. A second strip of fibrous composition was placed on top of the die plate. Pressure was applied to cut and bond the edges of the first and second fibrous composition layers. The dose was removed the die cutter and the process was repeated for each dose.

TABLE 1

Fibrous Unit-Dose Compositions

| Location | Ingredient | Ex. 1 (% total wt) | Ex. 2 (% total wt) | Ex. 3 (% total wt) |
|---|---|---|---|---|
| Fibrous Composition | Sodium Lauryl Sulfate | 6.35 | 7.31 | 5.70 |
| | Cocamidopropyl Betaine | 0.32 | 2.14 | 0.29 |
| | Polyvinyl Alcohol[1] | 10.80 | 8.66 | 9.91 |
| | Sodium Saccharin | 1.27 | 1.22 | 1.14 |
| | Xylitol | 5.97 | — | — |
| | Sorbitol | — | 0.43 | 5.35 |
| | Sucralose | 0.08 | — | 0.07 |
| | NaF | — | — | — |
| | SnF$_2$ | — | 1.46 | — |
| | Sodium Gluconate | — | 3.29 | — |
| Nonfibrous Composition | PEG 600 | 19.67 | 19.93 | 20.49 |
| | Silica | 32.78 | 33.21 | 34.15 |
| | Sodium Hexametaphosphate | 16.39 | 16.61 | 17.07 |
| | Flavors/Dyes | 5.56 | 4.98 | 5.13 |
| | NaF | — | — | 0.30 |

[1]Mixture of PVA403 and PVA 420H

TABLE 2

Oral Care Compositions

| | Ex. 1 | Ex. 2 | Ex. 3 | 3DW | 3DW + Surfactants | W + S | Colgate ®* |
|---|---|---|---|---|---|---|---|
| Total Surfactant Level per Dose (mg) | 34.0 | 32.5 | 29.9 | 20.3 | 35.2 | 37.3 | 14.6 | 11.6-23.2 |
| Dose Size (mg) | 305.0 | 301.1 | 292.8 | 1000.0 | 1000.0 | 1058.5 | 1000.0 | 1000.0 |
| Total Surfactant (wt %) | 11.1 | 10.8 | 10.2 | 2.0 | 3.4 | 3.4 | 1.5 | 1.2-2.3 |
| SLS (wt %) | 10.8 | 8.7 | 9.9 | 2.0 | 3.4 | 3.4 | 1.5 | 1.2-2.3 |
| Betaine (wt %) | 0.3 | 2.1 | 0.3 | — | 0.1 | 0.1 | — | — |
| Polysorbate 80 (wt %) | — | — | — | — | — | — | 0.006 | — |

*Surfactant level is provided as a range as surfactant levels are not provided in the product information.

TABLE 2 describes the oral care compositions used in the foam volume testing shown in TABLE 3. Ex. 1-3 are unit-dose dentifrice compositions with a total surfactant level of between 30 mg and 35 mg with a dose size of approximately 300 mg. Ex. 1-3 have a mixture of sodium lauryl sulfate and cocamidopropyl betaine as the surfactants. The unit-dose dentifrice compositions are compared with three commercially available dentifrice compositions: Crest® 3D White—Radiant Mint (3DW), Crest® Whitening+Scope® (W+S), and Colgate® Total® Whitening (Colgate®). Additionally, a sample of 3DW was combined with additional portions of surfactants to have an approximately equivalent amount and identity of surfactants as Ex. 1-3 per dose (3DW+Surfactants). Upon mixing the 3DW+Surfactants sample displayed an increased viscosity to a degree that would make the sample unsuitable for use in an extrudable dentifrice tube, the typical dentifrice dispenser.

Foam volume was then determined by measuring the volume of foam generated after blending a slurry of the dentifrice in water. A slurry of dentifrice in water was created by added the selected volume (from TABLE 3) to a single unit-dose of dentifrice (for Ex. 1, Ex. 2, and Ex. 3) or the equivalent dose of paste dentifrice for commercial formulations at 32° C. The mixture of dentifrice and water was manually mixed with a spatula to reach homogeneity while minimizing aeration. The homogenous dentifrice-water slurry was transferred to a 500 mL graduated cylinder retrofitted with a shear device from a Waring commercial blender (Waring, Torrington, Conn., #33BL12), as in FIG. 1. The blender was turned on "HIGH" for 10 seconds. The blending was stopped, and the slurry was allowed to rest for 5 seconds prior to reading the foam volume. The foam volume increase (%) was calculated by dividing the volume of the foam by the starting volume and multiplying the quotient by 100, this value is reported in TABLE 3. The surfactant % in TABLE 2 was calculated based on the total surfactant present in the composition tested and how much water was added to the dentifrice-water slurry.

Figure 2:
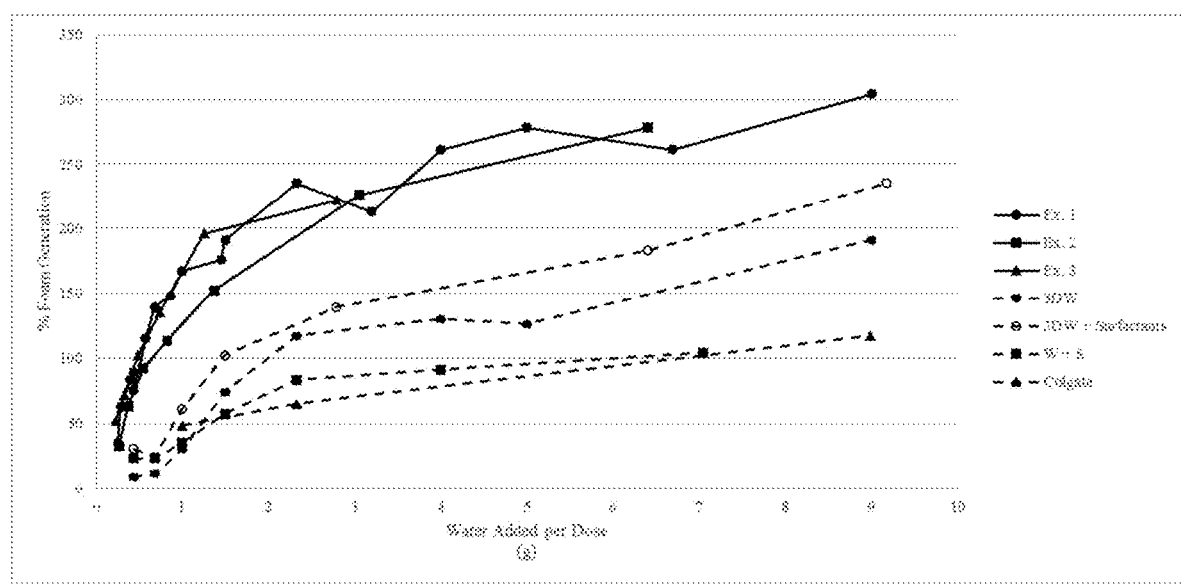
FIG. 2 is a graph illustrating the increase in foam volume as a function of water added.
Figure 3:
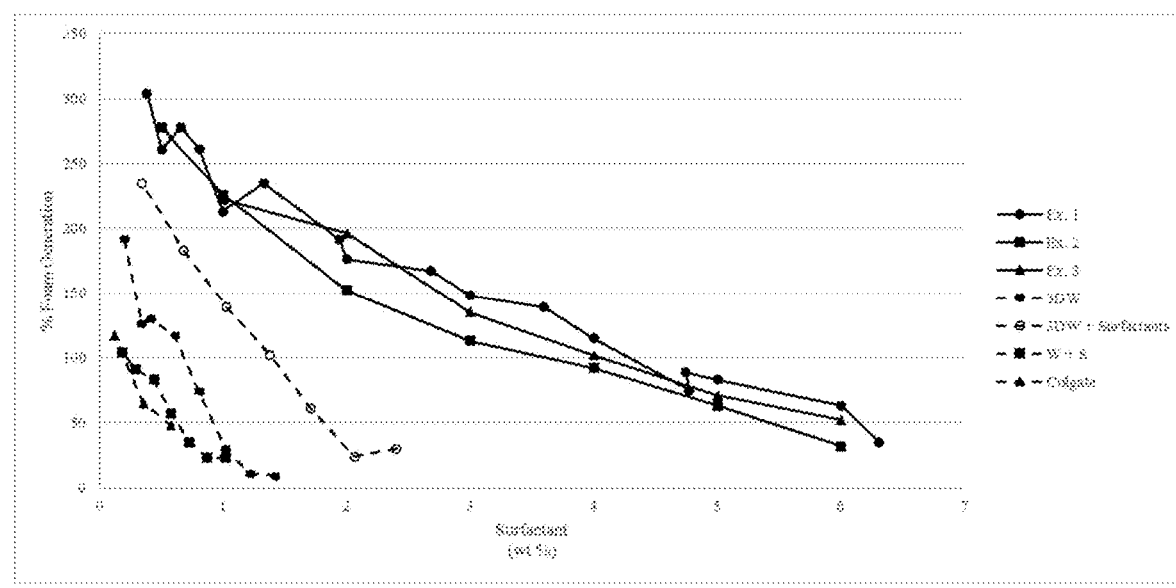
FIG. 3 is a graph illustrating the increase in foam volume as a function of the total amount of surfactant.
Figure 4:
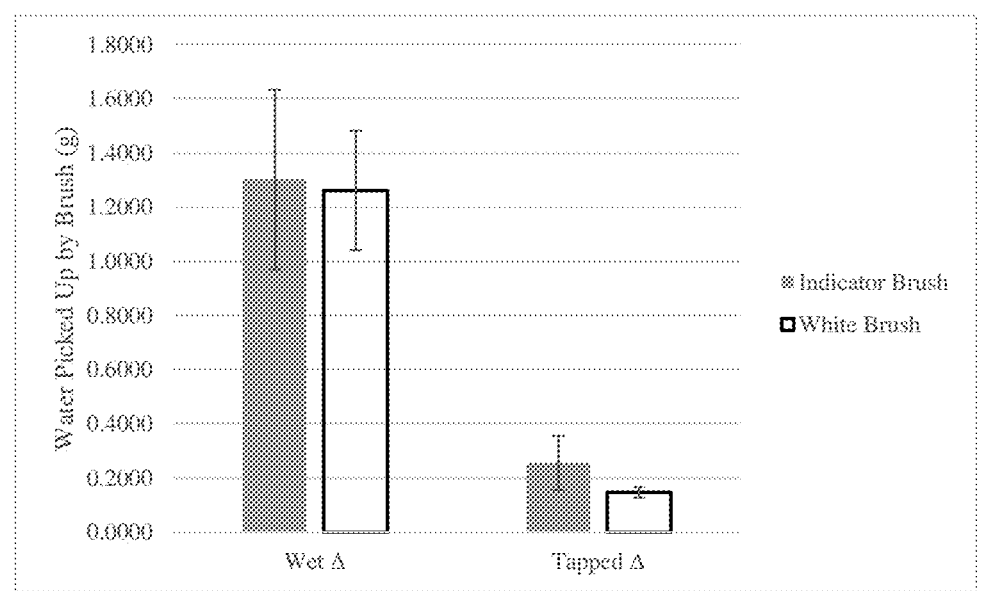
FIG. 4 is a graph illustrating the amount of water absorbed by a toothbrush.

Between the concentrations measured, the more dilute the system, the more foam is generated. Ex. 1, Ex. 2, and Ex. 3 all displayed similar foam results at much higher volumes than achievable with commercial products, see TABLE 3 and FIG. 2 and FIG. 3. Additionally, Ex. 1-3, all displayed higher foaming efficiency (volume foam per mass of surfactant) than 3DW+Surfactants despite having a roughly equivalent amount of surfactant per dose (~30-35 mg). The dose amount is based on the amount of fluoride which is formulated to provide the amount of fluoride required by the FDA monograph for an anti-cavity benefit Foam generation is defined as the difference in volume of the foam head minus the starting liquid volume divided by the starting liquid volume. Typical ranges of water present during brushing is 0.1-2.0 g, as demonstrated by measuring water uptake by a brush and understanding of salivary flow during brushing, as displayed in TABLE 4, TABLE 5, and FIG. 4.

TABLE 3

| | Foam Generation | | | | | | | | | | | | |
|---|---|---|---|---|---|---|---|---|---|---|---|---|---|
| | Ex. 1 | | Ex. 2 | | Ex. 3 | | 3DW | | 3DW + Surfactants | | W + S | | Colgate® |
| H$_2$O per Dose, g | Foam Gen., % | Surfactant, % | Foam Gen., % | Surfactant, % | Foam Gen., % | Surfactant, % | Foam Gen., % | Surfactant, % | Foam Gen., % | Surfactant, % | Foam Gen., % | Surfactant, % | Foam Gen., % | Surfactant, % |
| 0.22 | | | | | 52 | 6.00 | | | | | | | | |
| 0.25 | 35 | 6.31 | | | | | | | | | | | | |
| 0.26 | | | 32 | 6.00 | | | | | | | | | | |
| 0.28 | 63 | 6.00 | | | | | | | | | | | | |
| 0.32 | | | | | 71 | 5.00 | | | | | | | | |
| 0.37 | | | 63 | 5.00 | | | | | | | | | | |
| 0.39 | 83 | 5.00 | | | | | | | | | | | | |
| 0.43 | 89 | 4.74 | | | | | 9 | 1.42 | 30 | 2.40 | 23 | 1.02 | | |
| 0.43 | 75 | 4.77 | | | | | | | | | | | | |
| 0.48 | | | | | 102 | 4.00 | | | | | | | | |
| 0.54 | | | 92 | 4.00 | | | | | | | | | | |
| 0.57 | 15 | 4.00 | | | | | | | | | | | | |
| 0.67 | 139 | 3.60 | | | | | 11 | 1.22 | 24 | 2.06 | 23 | 0.87 | | |
| 0.73 | | | | | 135 | 3.00 | | | | | | | | |
| 0.82 | | | 113 | 3.00 | | | | | | | | | | |
| 0.86 | 148 | 3.00 | | | | | | | | | | | | |
| 1.00 | 167 | 2.68 | | | | | 30 | 1.02 | 61 | 1.71 | 35 | 0.73 | 48 | 0.58 |
| 1.25 | | | | | 196 | 2.00 | | | | | | | | |
| 1.37 | | | 152 | 2.00 | | | | | | | | | | |
| 1.45 | 176 | 2.00 | | | | | | | | | | | | |
| 1.50 | 191 | 1.94 | | | | | 74 | 0.81 | 102 | 1.38 | 57 | 0.58 | | |
| 2.33 | 235 | 1.33 | | | | | 117 | 0.61 | | | 83 | 0.44 | 65 | 0.35 |
| 2.79 | | | | | 222 | 1.00 | | | 139 | 1.03 | | | | |
| 3.05 | | | 226 | 1.00 | | | | | | | | | | |
| 3.19 | 213 | 1.00 | | | | | | | | | | | | |
| 4.00 | 261 | 0.81 | | | | | 130 | 0.41 | | | 91 | 0.29 | | |
| 5.00 | 278 | 0.66 | | | | | 126 | 0.34 | | | | | | |
| 6.40 | | | 278 | 0.50 | | | | | 183 | 0.68 | | | | |
| 6.69 | 261 | 0.50 | | | | | | | | | | | | |
| 7.04 | | | | | | | | | | | 104 | 0.18 | | |
| 8.99 | | | | | | | | | | | | | 117 | 0.12 |
| 9.00 | | | | | | | 191 | 0.20 | | | | | | |
| 9.01 | 304 | 0.38 | | | | | | | | | | | | |
| 9.17 | | | | | | | | | 235 | 0.34 | | | | |

TABLE 4

Water picked up by dry Oral B Indicator Brush and generic white brush

|  | Oral B Indicator Brush | Generic White Brush |
|---|---|---|
| Wet (g) | 1.3023 | 1.2619 |
| Tapped (g) | 0.2558 | 0.1470 |
| Wet δ. | 0.3319 | 0.2206 |
| Tapped δ | 0.1001 | 0.0195 |

TABLE 5

Salivary Flow Rates.

|  | Salivary Flow Rates, g/min |
|---|---|
| Dry Mouth | 0.10 |
| Average Mouth | 0.20 |

A two-week consumer preference study was performed to determine whether consumer preferred the foam generated by the compositions disclosed herein or commercial paste products. As shown in TABLE 6 and TABLE 7, the consumers thought that the foam in the compositions disclosed herein was larger in volume, developed quickly, and was at least as thick as the foam generated from commercial paste products. Ex. 1 had just the right thickness compared with the commercial dentifrice formulations.

TABLE 6

Two Week Use Test

|  | Crest ® Whitening Plus Scope ® | Colgate ® Total Whitening | Ex. 1 |
|---|---|---|---|
| Base Size | 84 | 87 | 85 |
| Feels like product/foam is reaching all areas of my mouth | 64 | 62 | 85 |
| Provides a deep penetrating foam | 59 | 60 | 79 |
| Foam lasts the whole brushing | 68 | 67 | 86 |
| Provides long-lasting clean feeling | 62 | 55 | 74 |

TABLE 7

Attributes of Unit-Dose Oral Care Compositions

| Attributes | Total Responses | Crest ® Whitening Plus Scope ® B 84 | Colgate ® Total Whitening D 87 | Ex. 1 E 85 |
|---|---|---|---|---|
| Amount of foam while brushing | Much too little | 6% | 6% | 1% |
|  | Somewhat too little | 30% e | 31% e | 7% |
|  | Just right | 62% de | 48% | 40% |
|  | Somewhat too much | 1% | 13% b | 31% bd |
|  | Much too much | 1% | 2% | 21% bd |
|  | Mean | 0.381 e | 0.2471e | −0.6322 |
| How quickly foam develops | Much too fast | 1% | 1% | 9% bd |
|  | Somewhat too fast | 4% | 4% | 7% |
|  | Just right | 75% | 68% | 78% |
|  | Somewhat too slowly | 13% | 20% e | 6% |
|  | Much too slowly | 7% e | 7% e | 0% |
|  | Mean | −0.2143 | −0.2824 | 0.1954 bd |
| Thickness of foam while brushing | Much too light/airy | 6% | 1% | 6% |
|  | Somewhat too light/airy | 30% de | 15% | 16% |
|  | Just right | 54% | 48% | 62% d |
|  | Somewhat too thick/heavy | 11% | 32% be | 12% |
|  | Much too thick/heavy | 0% | 4% | 5% |
|  | Mean | 0.3095 de | −0.2118 | 0.069 d |

TABLE 8

Cleaning Performance of Unit Dose Oral Care Compositions

| Product | RDA | PCR | PCR/RDA |
|---|---|---|---|
| Crest ® Complete Outlast Whitening + Scope ® | 199 ± 36.5 | — | — |
| Crest ® Cavity Protection | 137 ± 24.6 | 69 ± 9.3 | 0.50 |
| Ex. 4 | 208 ± 29.7 | 83 ± 3.4 | 0.40 |
| Ex. 5 | 278 ± 32.9 | 92 ± 18.1 | 0.33 |
| Ex. 6 | 225 ± 32.6 | 108 ± 8.2 | 0.48 |

TABLE 9

Unit-Dose Oral Care Compositions

| Location | Ingredient | Ex. 4 (% total wt) | Ex. 5 (% total wt) | Ex. 6 (% total wt) |
|---|---|---|---|---|
| Fibrous Composition | Sodium Lauryl Sulfate | 14.77 | 12.82 | 10.95 |
|  | Cocamidopropyl Betaine | 0.44 | 0.38 | 0.33 |
|  | Polyvinyl Alcohol[1] | 8.68 | 7.54 | 6.4 |
|  | Sodium Saccharin | 1.31 | 1.51 | 1.29 |
|  | Xylitol | 6.16 | 7.09 | 6.05 |
|  | Sucralose | 0.08 | 0.09 | 0.08 |

TABLE 9-continued

Unit-Dose Oral Care Compositions

| Location | Ingredient | Ex. 4 (% total wt) | Ex. 5 (% total wt) | Ex. 6 (% total wt) |
|---|---|---|---|---|
| Nonfibrous Composition | PEG-12 | 15.22 | 16.98 | 20.63 |
| | Silica | 21.74 | 28.30 | 31.56 |
| | Sodium Hexametaphosphate | 21.74 | 18.87 | 16.61 |
| | Flavors/Dyes | 7.18 | 6.41 | 5.64 |
| | NaF | — | — | 0.30 |

[1]Mixture of PVA403 and PVA 420H

Cleaning

The Pellicle Cleaning Ratio (PCR) is a measure of the cleaning characteristics of a dentifrice. Relative Dentine Abrasion value (RDA) is a measure of the abrasiveness of a dentifrice. PCR and RDA values are presented in TABLE 8. Ex. 4-6 all had a higher PCR value than Crest® Cavity Protection (CCP, 69. Additionally, Ex. 4-6 had higher RDA values than CCP. The PCR/RDA ratio is an indication of cleaning performance relative to abrasiveness. Ex. 6 has the greatest PCR/RDA ratio (0.48), only slightly below CCP (0.50).

Pellicle Cleaning Ratio (PCR)

The PCR according to TABLE 8 was determined by an in vitro model for evaluating the cleaning ability of dentifrices and abrasive powders. First, stained teeth were obtained. Next, the stained teeth were subsequently treated with a dentifrice with an abrasive. Finally, the stain removal performance was evaluated by comparing an image of the tooth before and after treatment.

Stained PCR chips were obtained directly from a supplier (stained PCR chips from Therametric Technologies, Inc., Noblesville, Ind.). Each tooth was stained in accordance with procedures described in Stookey et al. In vitro Removal of Stain with Dentifrices. *J. Dent. Res.* 61 (1982) 1236-1239 and Schemehorn et al. Abrasion, Polishing, and Stain Removal Characteristics of Various Commercial Dentifrices In Vitro. *J. Clinical Dent.* 22 (2011) 11-18, which are herein incorporated by reference.

The stained bovine teeth were imaged with a digital camera to determine the starting values for L (lightness), a (red/green coordinate) and b (yellow/blue coordinate). The stained teeth were randomized and treated with a selected composition.

Dentifrice slurries were prepared by diluting 25 g of the selected dentifrice composition with 40 g of ultrapure distilled water. Dentifrice slurries were compared to a calcium pyrophosphate standard slurry prepared by combining 10 g of calcium pyrophosphate (Model No. A27672, Odontex Solutia, St. Louis, Mo.) with 50 g of a solution containing 0.5 wt % of carboxymethylcellulose (Model No. CA192, Spectrum Chemicals, New Brunswick, N.J.) and 10 wt % of glycerol (Model No. GX0185-6, EMD, Burlington, Mass.).

Samples were secured on each station of a V-8 brushing machine (Sabri Dental Enterprises, Downers Grove, Ill.). The tension of each brush was adjusted to 150 g by loosening or tightening the spring tension screws on the V-8 brushing machine. The brushes used were ADA40 Brushes. The slurry solutions were attached to each brushing station. The V-8 brush machine was set to 800 strokes at 50 strokes/18 sec.

Samples were collected from the brushing machine and rinsed with tap water. Samples were imaged to determine final values for L (lightness), a (red/green coordinate) and b (yellow/blue coordinate). The PCR was determined using Formula 1.

PCR Calculation $$PCR = \frac{\Delta L \text{ of specimen after 800 stroke cleaning with selected paste}}{\text{Average } \Delta L \text{ of calcium pyrophosphate standard after 800 stroke cleaning}} \times 100 \quad \text{Formula 1}$$

Relative Dentin Abrasion (RDA)

The Relative Dentin Abrasion (RDA) test is typically performed to confirm that a dentifrice composition, e.g., toothpaste, is safe for consumer use, with the upper limit of the test set at 250. The RDA according to TABLE 7 was determined by using the industrial published standard as outlined in FDIS-ISO 11609, Annexure, third edition Annex B: Determination of relative dentifrice abrasivity to enamel and dentine by a surface profile method, which is herein incorporated by reference. This method is based on the determination of abraded depth after brushing using profilometry.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A solid unit-dose oral care composition comprising:
   (a) fibrous composition comprising:
      (i) from about 1% to about 25%, by weight of the unit-dose oral care composition, of web forming material, the web forming material comprising polyvinyl alcohol;
      (ii) from about 0.01% to about 20%, by weight of the unit-dose oral care composition, of surfactant, and
      (iii) sugar alcohol;
   (b) nonfibrous composition comprising abrasive.

2. The unit-dose oral care composition of claim 1, wherein the surfactant comprises anionic surfactant, zwitterionic surfactant, or combinations thereof.

3. The unit-dose oral care composition of claim 1, wherein the surfactant comprises sodium lauryl sulfate, cocamidopropyl betaine, or combinations thereof.

4. The unit-dose oral care composition of claim 1, wherein the oral care composition comprises a fluoride ion source, stannous ion source, zinc ion source, or combinations thereof.

5. The unit-dose oral care composition of claim 1, wherein the unit-dose oral care composition comprises from about 0.01% to about 50%, by weight of the unit-dose oral care composition, of the sugar alcohol.

6. The unit-dose oral care composition of claim 5, wherein the sugar alcohol comprises sorbitol, mannitol, lactitol, isomalt, arabitol, erythritol, glycerol, maltitol, xylitol, or combinations thereof.

7. The unit-dose oral care composition of claim 5, wherein the sugar alcohol comprises xylitol, sorbitol, glycerin, or combinations thereof.

8. The unit-dose oral care composition of claim 1, wherein the abrasive comprises a calcium-containing abrasive, silica abrasive, carbonate abrasive, phosphate abrasive, alumina abrasive, or combinations thereof.

9. The unit-dose oral care composition of claim 1, wherein at least a portion of the nonfibrous composition is in contact with a surface of the fibrous composition.

10. The unit-dose oral care composition of claim 4, wherein the fluoride ion source comprises stannous fluoride, sodium fluoride, potassium fluoride, amine fluoride, sodium monofluorophosphate, zinc fluoride, or combinations thereof.

11. The unit-dose oral care composition of claim 4, wherein the stannous ion source comprises stannous fluoride, stannous chloride, or combinations thereof.

12. The unit-dose oral care composition of claim 4, wherein the zinc ion source comprises zinc citrate, zinc chloride, zinc sulfate, zinc gluconate, zinc lactate, zinc phosphate, zinc arginine, zinc fluoride, zinc iodide, zinc carbonate, or combinations thereof.

13. The unit-dose oral care composition of claim 4, wherein the fibrous composition comprises the fluoride ion source, the stannous ion source, the zinc ion source, or combinations thereof.

14. The unit-dose oral care composition of claim 4, wherein the nonfibrous composition comprises the fluoride ion source, the stannous ion source, the zinc ion source, or combinations thereof.

* * * * *